(12) United States Patent
Martinez et al.

(10) Patent No.: US 8,129,330 B2
(45) Date of Patent: Mar. 6, 2012

(54) POLYMER CONJUGATES WITH DECREASED ANTIGENICITY, METHODS OF PREPARATION AND USES THEREOF

(75) Inventors: Alexa L Martinez, San Jose, CA (US); Merry R Sherman, San Carlos, CA (US); Mark G. P. Saifer, San Carlos, CA (US); L. David Williams, Fremont, CA (US)

(73) Assignee: Mountain View Pharmaceuticals, Inc., Menlo Park, CA (US)

( * ) Notice: Subject to any disclaimer, the term of this patent is extended or adjusted under 35 U.S.C. 154(b) by 2066 days.

(21) Appl. No.: 10/669,597

(22) Filed: Sep. 25, 2003

(65) Prior Publication Data

US 2004/0062746 A1  Apr. 1, 2004

Related U.S. Application Data

(63) Continuation-in-part of application No. 10/317,092, filed on Dec. 12, 2002, now abandoned.

(60) Provisional application No. 60/414,424, filed on Sep. 30, 2002.

(51) Int. Cl.
*A61K 38/04* (2006.01)
*A61K 38/16* (2006.01)

(52) U.S. Cl. ...... 514/1.1; 514/21.2; 514/21.3; 514/21.4; 514/21.5; 514/21.6; 530/324; 530/350

(58) Field of Classification Search .......... None
See application file for complete search history.

(56) References Cited

U.S. PATENT DOCUMENTS

| | | | |
|---|---|---|---|
| 3,960,830 A | 6/1976 | Bayer et al. ........... 206/112.5 R |
| 4,002,531 A | 1/1977 | Royer | |
| 4,088,538 A | 5/1978 | Schneider ................. 195/63 |
| 4,179,337 A | 12/1979 | Davis et al. | |
| 4,261,973 A | 4/1981 | Lee et al. | |
| 4,301,144 A | 11/1981 | Iwashita et al. ............. 424/78 |
| 4,434,228 A | 2/1984 | Swann | |
| 4,609,546 A | 9/1986 | Hiratani | |
| RE32,518 E | 10/1987 | Miyasaka et al. | |
| 4,902,502 A | 2/1990 | Nitecki et al. | |
| 4,904,582 A | 2/1990 | Tullis | |
| 4,917,888 A | 4/1990 | Katre et al. ............. 424/85.91 |
| 4,943,579 A | 7/1990 | Vishnuvajjala et al. | |
| 4,946,778 A | 8/1990 | Ladner et al. | |
| 5,004,605 A | 4/1991 | Hershenson et al. | |
| 5,004,758 A | 4/1991 | Boehm et al. | |
| 5,006,333 A | 4/1991 | Saifer et al. | |
| 5,013,556 A | 5/1991 | Woodle et al. | |
| 5,037,969 A | 8/1991 | Minami et al. | |
| 5,080,891 A | 1/1992 | Saifer et al. | |
| 5,089,261 A | 2/1992 | Nitecki et al. | |
| 5,093,531 A | 3/1992 | Sano et al. | |
| 5,183,660 A | 2/1993 | Ikeda et al. | |
| 5,252,714 A | 10/1993 | Harris et al. | |
| 5,283,317 A | 2/1994 | Saifer et al. | |
| 5,286,637 A | 2/1994 | Veronese et al. | |
| 5,349,052 A * | 9/1994 | Delgado et al. ............. 530/351 |
| 5,395,619 A | 3/1995 | Zalipsky et al. | |
| 5,428,128 A | 6/1995 | Mensi-Fattohi et al. | |
| 5,468,478 A | 11/1995 | Saifer et al. | |
| 5,476,653 A | 12/1995 | Pitt et al. | |
| 5,612,460 A | 3/1997 | Zalipsky | |
| 5,621,039 A | 4/1997 | Hallahan et al. | |
| 5,622,986 A | 4/1997 | Greenwald et al. | |
| 5,643,575 A | 7/1997 | Martinez et al. | |
| 5,672,662 A | 9/1997 | Harris et al. | |
| 5,728,560 A | 3/1998 | Shorr et al. | |
| 5,730,990 A | 3/1998 | Greenwald et al. | |
| 5,738,846 A | 4/1998 | Greenwald et al. | |
| 5,766,897 A | 6/1998 | Braxton | |
| 5,811,076 A | 9/1998 | Brasch et al. | |
| 5,824,701 A | 10/1998 | Greenwald et al. | |
| 5,840,900 A | 11/1998 | Greenwald et al. | |
| 5,880,131 A | 3/1999 | Greenwald et al. | |
| 5,880,225 A | 3/1999 | Yang et al. | |
| 5,880,255 A | 3/1999 | Delgado et al. | |
| 5,900,402 A | 5/1999 | Shorr | |
| 5,902,588 A | 5/1999 | Greenwald et al. | |
| 5,919,455 A | 7/1999 | Greenwald et al. | |
| 5,932,462 A | 8/1999 | Harris et al. | |
| 5,935,564 A | 8/1999 | Seely | |

(Continued)

FOREIGN PATENT DOCUMENTS

EP    0 377 613 B1    12/1992
(Continued)

OTHER PUBLICATIONS

Veronese M. F. "Peptide and Protein PEGylation: a review of problems and solutions." Biomaterials. vol. 22, pp. 405-417 (2001).*
Roberts et al. "Chemistry for proetin and peptide PEGylation." Advanced Drug Delivery Reviews. vol. 54 (2202) 459-476.*
Nagasaki, Y., et al., "Formyl-Ended Heterobifunctional Poly(ethylene oxide): Synthesis of Poly(ethylene oxide) with a Formyl Group at One End and a Hydroxyl Group at the Other End," *Bioconjug. Chem.* 6:231-233, American Chemical Society (1995).
International Search Report for corresponding International Application No. PCT/US03/29989, mailed May 24, 2005.
Abuchowski, A., and Davis, F.F., "Soluble Polymer-Enzyme Adducts," in *Enzymes as Drugs*, Holcenberg, J.S., et al., eds., John Wiley & Sons, Inc., New York, NY, pp. 367-383, (1981).
Abuchowski, A., et al., "Cancer Therapy with Chemically Modified Enzymes. I. Antitumor Properties of Polyethylene Glycol-Asparaginase Conjugates," *Cancer Biochem. Biophys.* 7:175-186, Gordon and Breach Science Publishers, Inc. (1984).

(Continued)

*Primary Examiner* — Anish Gupta
(74) *Attorney, Agent, or Firm* — Sterne, Kessler, Goldstein & Fox P.L.L.C.

(57) ABSTRACT

Methods are provided for the preparation of conjugates of a variety of bioactive components, especially proteins, with water-soluble polymers (e.g., poly(ethylene glycol) and derivatives thereof), which conjugates have reduced antigenicity and immunogenicity compared to similar conjugates prepared using poly(ethylene glycol) containing a methoxyl or another alkoxyl group. The invention also provides conjugates prepared by such methods, compositions comprising such conjugates, kits containing such conjugates or compositions and methods of use of the conjugates and compositions in diagnostic and therapeutic protocols.

94 Claims, 9 Drawing Sheets

U.S. PATENT DOCUMENTS

| | | | |
|---|---|---|---|
| 5,951,974 | A | 9/1999 | Gilbert et al. |
| 5,965,119 | A | 10/1999 | Greenwald et al. |
| 5,965,566 | A | 10/1999 | Greenwald et al. |
| 5,969,040 | A | 10/1999 | Hallahan et al. |
| 5,981,709 | A | 11/1999 | Greenwald et al. |
| 5,990,237 | A | 11/1999 | Bentley et al. |
| 6,011,042 | A | 1/2000 | Greenwald et al. |
| 6,042,822 | A | 3/2000 | Gilbert et al. |
| 6,113,906 | A | 9/2000 | Greenwald et al. |
| 6,127,355 | A | 10/2000 | Greenwald et al. |
| 6,132,713 | A | 10/2000 | Fiipula et al. |
| 6,132,763 | A | 10/2000 | Fisher |
| 6,177,087 | B1 | 1/2001 | Greenwald et al. |
| 6,180,095 | B1 | 1/2001 | Greenwald et al. |
| 6,180,134 | B1 | 1/2001 | Zalipsky et al. ............ 424/450 |
| 6,239,262 | B1 | 5/2001 | Cramer et al. |
| 6,245,901 | B1 | 6/2001 | von der Osten et al. |
| 6,552,167 | B1 | 4/2003 | Rose |
| 6,566,506 | B2 | 5/2003 | Greenwald et al. |
| 6,576,134 | B1 | 6/2003 | Agner |
| 6,576,235 | B1 | 6/2003 | Williams et al. |
| 6,596,849 | B1 | 7/2003 | Roffler et al. |
| 6,617,118 | B2 | 9/2003 | Roffler et al. |
| 6,638,500 | B1 | 10/2003 | El-Tayar et al. |
| 6,783,965 | B1 | 8/2004 | Sherman et al. |
| 6,824,782 | B2 | 11/2004 | Whitlow et al. |
| 6,864,327 | B2 | 3/2005 | Bentley et al. |
| 6,887,462 | B2 | 5/2005 | Shirley et al. |
| 2001/0028881 | A1 | 10/2001 | Roffler et al. |
| 2002/0052443 | A1 | 5/2002 | Greenwald et al. |
| 2002/0061307 | A1 | 5/2002 | Whitlow et al. |
| 2002/0072573 | A1 | 6/2002 | Bentley et al. |
| 2002/0098192 | A1 | 7/2002 | Whitlow et al. |
| 2003/0012777 | A1 | 1/2003 | Sherman et al. |
| 2003/0082786 | A1 | 5/2003 | Ensor et al. |
| 2003/0153694 | A1 | 8/2003 | Rosen et al. |
| 2004/0034188 | A1 | 2/2004 | Rosen et al. |
| 2004/0062746 | A1 | 4/2004 | Martinez et al. |
| 2005/0054816 | A1 | 3/2005 | McManus et al. |
| 2007/0185135 | A1 | 8/2007 | Wu et al. |

FOREIGN PATENT DOCUMENTS

| | | |
|---|---|---|
| EP | 1 037 657 B1 | 9/2000 |
| EP | 0 730 470 B1 | 3/2002 |
| EP | 1 107 998 B1 | 2/2004 |
| EP | 0 822 199 B1 | 9/2004 |
| EP | 1 656 410 B1 | 5/2006 |
| IL | 142282 | 8/2007 |
| JP | 55-99189 A | 7/1980 |
| WO | WO 87/06838 A1 | 11/1987 |
| WO | WO 89/01033 A1 | 2/1989 |
| WO | WO 90/04606 A1 | 5/1990 |
| WO | WO 91/07190 A1 | 5/1991 |
| WO | WO 92/19273 A1 | 11/1992 |
| WO | WO 95/00162 A1 | 1/1995 |
| WO | WO 95/13090 A1 | 5/1995 |
| WO | WO 95/32003 A1 | 11/1995 |
| WO | WO 95/34326 * | 12/1995 |
| WO | WO 98/48837 A1 | 11/1998 |
| WO | WO 99/03887 A1 | 1/1999 |
| WO | WO 99/32140 A1 | 7/1999 |
| WO | WO 99/45026 A1 | 9/1999 |
| WO | WO 00/07629 A3 | 2/2000 |
| WO | WO 00/12587 A2 | 3/2000 |
| WO | WO 00/23114 A2 | 4/2000 |
| WO | WO 00/23114 A3 | 4/2000 |
| WO | WO 00/23798 A1 | 4/2000 |
| WO | WO 00/42175 A1 | 7/2000 |
| WO | WO 01/26692 A1 | 4/2001 |
| WO | WO 01/41812 A2 | 6/2001 |
| WO | WO 01/59078 A2 | 8/2001 |
| WO | WO 01/87925 A2 | 11/2001 |
| WO | WO 02/094853 A2 | 11/2002 |
| WO | WO 03/002716 A2 | 1/2003 |
| WO | WO 03/011211 A2 | 2/2003 |
| WO | WO 03/061577 A2 | 7/2003 |
| WO | WO 2004/030617 A2 | 4/2004 |

OTHER PUBLICATIONS

Abuchowski, A., et al., "Effect of Covalent Attachment of Polyethylene Glycol on Immunogenicity and Circulating Life of Bovine Liver Catalase," *J. Biol. Chem.* 252:3582-3586, American Society of Biological Chemists, Inc. (1977).

Akiyama, Y., et al., "Selective Synthesis of Heterobifunctional Poly(ethylene glycol) Derivatives Containing Both Mercapto and Acetal Terminals," *Bioconj. Chem.* 11:947-950, American Chemical Society (2000).

Arakawa, T., et al., "Reversibility of Acid Denaturation of Recombinant Interferon-γ," *Biopolymers* 29:1065-1068, John Wiley & Sons, Inc. (1990).

Beauchamp. C.O., et al., "A New Procedure for the Synthesis of Polyethylene Glycol-Protein Adducts; Effects on Function, Receptor Recognition, and Clearance of Superoxide Dismutase, Lactoferrin, and $\alpha_2$-Macroglobulin," *Anal. Biochem.* 131:25-33, Academic Press, Inc. (1983).

Benhar, I., et al., "Mutations of Two Lysine Residues in the CDR Loops of a Recombinant Immunotoxin That Reduce Its Sensitivity to Chemical Derivatization," *Bioconj. Chem.* 5:321-326, American Chemical Society (1994).

Bentley, M.D., et al., "Reductive Amination Using Poly(ethylene glycol) Acetaldehyde Hydrate Generated in Situ: Applications to Chitosan and Lysozyme," *J. Pharm. Sci.* 87:1446-1449, American Chemical Society and American Pharmaceutical Association (1998).

Blake, M.S., et al., "A Rapid, Sensitive Method for Detection of Alkaline Phosphatase-Conjugated Anti-antibody on Western Blots," *Anal. Biochem.* 136:175-179, Academic Press, Inc. (1984).

Brenner, B.M., et al., "Glomerular permselectivity: barrier function based on discrimination of molecular size and charge," *Am. J. Physiol.* 234:F455-F460, American Physiological Society (1978).

Cheng, T.-L., et al., "Efficient Clearance of Poly(ethylene glycol)-Modified Immunoenzyme with Anti-PEG Monoclonal Antibody for Prodrug Cancer Therapy," *Bioconj. Chem.* 11:258-266, American Chemical Society (2000).

Cheng, T.-L., et al., "Accelerated Clearance of Polyethylene Glycol-Modified Proteins by Anti-Polyethylene Glycol IgM," *Bioconj. Chem.* 10:520-528, American Chemical Society (1999).

Clark, R., et al., "Long-acting Growth Hormones Produced by Conjugation with Polyethylene Glycol," *J. Biol. Chem.* 271:21969-21977, The American Society for Biochemistry and Molecular Biology, Inc. (1996).

Davis, S., et al., "Alteration of the circulating life and antigenic properties of bovine adenosine deaminase in mice by attachment of polyethylene glycol," *Clin. Exp. Immunol.* 46:649-652, Blackwell Scientific Publications (1981).

Fuke, I., et al., "Synthesis of poly(ethylene glycol) derivatives with different branchings and their use for protein modification," *J. Control. Rel.* 30:27-34, Elsevier Science B.V. (1994).

Harris. J.M., et al., "Synthesis and Characterization of Poly(ethylene glycol) Derivatives," *J. Polymer Sci.* 22:341-352, John Wiley & Sons, Inc. (1984).

Hershfield, M.S., et al., "Treatment of Adenosine Deaminase Deficiency with Polyethylene Glycol-Modified Adenosine Deaminase," *N. Engl. J. Med.* 316:589-596, Massachusetts Medical Society (1987).

Iakunitskaia, L.M., et al., "Preparation of Subtilisin BPN' and Dextrane Conjugates," *Prikl. Biokhim. Mikrobiol.* 16:232-237, Nauka (1980).

Kelly, S.J., et al., "Diabetes Insipidus in Uricase-Deficient Mice: A Model for Evaluating Therapy with Poly(Ethylene Glycol)-Modified Uricase," *J. Am. Soc. Nephrol.* 12:1001-1009, Lippincott Williams & Wilkins (May 2001).

Kocienski, P.J., "2.4.4 Trityl Ethers," in *Protecting Groups, 1st edition*, Georg Thieme Verlag, Stuttgart, Germany, pp. 54-55 and 260 (1994).

Kito, M., et al., "A Simple and Efficient Method for Preparation of Monomethoxypolyethylene Glycol Activated with *p*-Nitrophenylchloroformate and Its Application to Modification of L-Asparaginase," *J. Clin. Biochem. Nutr.* 21:101-111, Institute of Applied Biochemistry (1996).

Kuwabara, T., et al., "Renal Clearance of a Recombinant Granulocyte Colony-Stimulating Factor, Nartograstim, in Rats," *Pharm. Res.* 12:1466-1469, Plenum Publishing Corporation (1995).

Marie, A., et al., "Characterization of Synthetic Polymers by MALDI-TOF/MS: Investigation into New Methods of Sample Target Preparation and Consequence on Mass Spectrum Finger Print," *Anal. Chem.* 72:5106-5114, American Chemical Society (2000).

Merrill, E.W., "Poly(ethylene oxide) star molecules: Synthesis, characterization, and applications in medicine and biology," *J. Biomater. Sci. Polymer Edn.* 5:1-11, VSP (1993).

Mordenti, J., et al., "Interspecies Scaling of Clearance and Volume of Distribution Data for Five Therapeutic Proteins," *Pharm. Res.* 8:1351-1359, Plenum Publishing Corporation (1991).

Narhi, L.O., et al., "Stoichiometric Complexation of Streptomyces Subtilisin Inhibitor and Subtilisin," *J. Prot. Chem.* 10:385-389, Plenum Publishing Corporation (1991).

Pui, C.-H., et al., "Recombinant Urate Oxidase for the Prophylaxis or Treatment of Hyperuricemia in Patients With Leukemia or Lymphoma," *J. Clin. Oncol.* 19:697-704, American Society of Clinical Oncology (Feb. 2001).

Richter, A.W., and Akerblom, E., "Antibodies against Polyethylene Glycol Produced in Animals by Immunization with Monomethoxy Polyethylene Glycol Modified Proteins," *Int. Archs. Allergy Appl. Immunol.* 70:124-131, S. Karger AG (1983).

Rocca, M., et al., "Pathophysiological and histomorphological evaluation of polyacryloylmorpholine vs polyethylene glycol modified superoxide dismutase in a rat model of ischaemia/reperfusion injury," *Int. J. Artif. Organs* 19:730-734, Wichtig Editore (1996).

Saifer, M.G.P., et al., "Improved Conjugation of Cytokines Using High Molecular Weight Poly(ethylene glycol): PEG-GM-CSF as a Prototype," *Polymer Preprints* 38:576-577, American Chemical Society (1997).

Sakane, T., and Pardridge, W.M., "Carboxyl-directed Pegylation of Brain-derived Neurotrophic Factor Markedly Reduces Systemic Clearance with Minimal Loss of Biologic Activity," *Pharm. Res.* 14:1085-1091, Plenum Publishing Corporation (1997).

Sayle, R.A., and Milner-White, E.J., "RASMOL: bimolecular graphics for all," *Trends Biochem. Sci.* 20:374-376, International Union of Biochemistry and Molecular Biology (1995).

Sharp, K.A., et al., "Synthesis and Application of a Poly(ethylene glycol)-Antibody Affinity Ligand for Cell Separations in Aqueous Polymer Two-Phase Systems," *Anal. Biochem.* 154:110-117, Academic Press, Inc. (1986).

Sherman, M.R., et al., "Conjugation of High-Molecular Weight Poly(ethylene glycol) to Cytokines: Granulocyte-Macrophage Colony-Stimulating Factors as Model Substrates," in *Poly(ethylene glycol): Chemistry and Biological Applications*, Harris, J.M., and Zalipsky, S., eds., American Chemical Society, Washington, DC, pp. 155-169 (1997).

Suzuki, T., et al., "Physicochemical and Biological Properties of Poly(ethylene glycol)-Coupled Immunoglobulin G," *Biochem. Biophys. Acta* 788:248-255, Elsevier Science B.V. (1984).

Tsai, N.-M., et al., "Sensitive Measurement of Polyethylene Glycol-Modified Proteins," *BioTechniques* 30:396-400 and 402, Eaton Publishing Co. (Feb. 2001).

Tsang, V.C.W., et al., "Calibration of Prestained Protein Molecular Weight Standards for Use in the 'Western' or Enzyme-Linked Immunoelectrotransfer Blot Techniques," *Anal. Biochem.* 143:304-307, Academic Press, Inc. (1984).

Venkatachalam, M.A., and Rennke, H.G., "The Structural and Molecular Basis of Glomerular Filtration," *Circ. Res.* 43:337-347, Grune & Stratton (1978).

Veronese, F.M., et al., "Surface Modification of Proteins. Activation of Monomethoxy-Polyethylene Glycols by Phenylchloroformates and Modification of Ribonuclease and Superoxide Dismutase," *Appl. Biochem. Biotech.* 11:141-152, The Humana Press Inc. (1985).

von Specht, B.-U., et al., "Polyvinylpyrrolidone as a Soluble Carrier of Proteins," *Hoppe-Seyler's Z. Physiol. Chem.* 354:1659-1660, Walter de Gruyter (1973).

Wilchek, M., et al., "Affinity Chromatography," *Meth. Enzymol.* 104:3-55, Academic Press, Inc. (1984).

Wilson, G., et al., "Selective Hepatic Uptake of Synthetic Glycoproteins. Mannosaminated Ribonuclease A Dimer and Serum Albumin," *J. Gen. Physiol.* 74:495-509, The Rockefeller University Press (1979).

Unverified English language abstract for Japanese Patent Publication No. 55-99189, Document AL1, Japan Patent Office (accessed via Internet on Aug. 9, 2002).

Tsutsumi, Y., et al., "Molecular design of hybrid tumour necrosis factor alpha with polyethylene glycol increases its anti-tumour potency," *Br. J. Cancer* 71:963-968, Stockton Press (1995).

Bailon., P. and Barthold, W., "Polyethylene glycol-conjugated pharmaceutical proteins," *PSTT* 1:352-356, Elsevier Science (1998).

Caliceti, P., et al., "Immunogenic and tolerogenic properties of monomethoxypoly(ethylene glycol) conjugated proteins," *Il Farmaco* 54:430-437, Elsevier (1999).

Clark, W.A., et al., "Site-specific $^{32}$P-labeling of cytokines, monoclonal antibodies, and other protein substrates for quantitative assays and therapeutic application," *Biotechniques Suppl*:76-87, Informa Healthcare USA, Inc. (Oct. 2002).

Hinds, K.D., and Kim, S.W., "Effects of PEG conjugation on insulin properties," *Adv. Drug Deliv. Rev.* 54:505-530, Elsevier Science Publishers, B.V. (Jun. 2002).

Koths, K., "Structure-function studies on human macrophage colony-stimulating factor (M-CSF)," *Mol. Reprod. Dev.* 46:31-38, Wiley-Liss (1997).

Lee, H., and Park, T.G., "Preparation and characterization of mono-PEGylated epidermal growth factor: evaluation of in vitro biologic activity," *Pharm. Res.* 19:845-851, Kluwer Academic/Plenum Publishers (Jun. 2002).

Pettit, D.K., et al., "Structure-function studies of interleukin 15 using site-specific mutagenesis, polyethylene glycol conjugation, and homology modeling," *J. Biol. Chem.* 272:2312-2318, American Society for Biochemistry and Molecular Biology (1997).

Daro, E., et al., "Polyethylene Glycol-Modified GM-CSF Expands CD11b$^{high}$CD11c$^{high}$ But Not CD11b$^{low}$CD11c$^{high}$ Murine Dendritic Cells In Vivo: A Comparative Analysis with Flt3 Ligand," *J. Immunol.* 165:49-58 (2000).

Gnanou, Y., and Rempp, P., "Macromonomer synthesis. New functionalization methods," *Makromol. Chem.* 188:2111-2119 (1987).

Gombotz, W.R., and Pettit, D.K., "Pegylation: A Tool To Enhance Protein Delivery," *Polymer Prepr.* 40:275-276 (1999).

Knüsli, C., et al., "Polyethylene glycol (PEG) modification of granulocyte-macrophage colony stimulating factor (GM-CSF) enhances neutrophil priming activity but not colony stimulating activity," *Br. J. Haematol.* 82:654-663 (1992).

Akerblom, Eva et al., "Preparation and Characterization of Conjugates of Monoclonal Antibodies and Staphylococcal Enterotoxin A using a New Hydrophilic Cross-Linker," *Bioconjugate Chem.* 4: 455-466, American Chemical Society (1993).

Ghedini, Nadia et al., "Synthesis and Partition Profiles of Nicotinic Acid Derivatives with Oligomeric Carriers," *Journal of Controlled Release* 3: 185-191, Elsevier Science Publishers B.V. (1986).

Johansson, Göte et al., "Preparation of Cibacron Blue F3G-A (Polyethylene Glycol) in Large Scale for Use in Affinity Partitioning," *Biotechnology and Bioengineering* XXVII: 621-625, John Wiley & Sons, Inc. (1985).

Khachadurian, Avedis K. et al., "Polyoxyethylated Cholesterol Derivatives, Organic Synthesis, Cellular Uptake and Effect on Lipid Metabolism in Cultured Skin Fibroblasts," *Biochimica et Biophysica Acta* 665: 434-441, Elsevier/North-Holland Biomedical Press (1981).

Maruyama, Kazuo et al., "Targetability of novel immunoliposomes modified with amphipathic poly(ethylene glycol)s conjugated at their distal terminals to monoclonal antibodies," *Biochimica et Biophysica Acta* 1234: 74-80, Elsevier Science B.V. (1995).

Nakamura, Teruo et al., "Synthesis of Heterobifunctional Poly(ethylene glycol) with a Reducing Monosaccharide Residue at One End," *Bioconjugate Chem.* 9: 300-303, American Chemical Society (1998).

Zalipsky, S. et al., "Attachment Of Drugs To Polyethylene Glycols," *Eur. Polym. J.* 19: 1177-1183, Pergamon Press Ltd. (1983).

Diwan, M. and Park, T.G., "Pegylation Enhances Protein Stability During Encapsulation in PGLA Microspheres," *Journal of Controlled Release* 73(2-3):233-44, Elsevier Science B.V., The Netherlands (Jun. 2001).

\* cited by examiner

*PEGylated fragment of CA II

POLYMER CONJUGATES WITH DECREASED ANTIGENICITY, METHODS OF PREPARATION AND USES THEREOF

CROSS REFERENCE TO RELATED APPLICATIONS

The present application is a continuation-in-part of U.S. application Ser. No. 10/317,092 filed Dec. 12, 2002, now abandoned, which claims the benefit of the filing date of U.S. Provisional Application No. 60/414,424, filed Sep. 30, 2002. The disclosures of the above-referenced applications are incorporated herein by reference in their entireties.

BACKGROUND OF THE INVENTION

1. Field of the Invention

The present invention is in the fields of protein biochemistry and the pharmaceutical and medical sciences. In particular, the invention provides methods for the production of conjugates between water-soluble polymers (e.g., poly(ethylene glycol) and derivatives thereof) and bioactive components, which conjugates have reduced antigenicity and immunogenicity compared to standard polymer-bioactive component conjugates. The invention also provides conjugates produced by such methods, compositions comprising such conjugates, kits comprising such conjugates and compositions and methods of use of the conjugates and compositions in preventing, diagnosing and treating a variety of medical and veterinary conditions.

2. Related Art

Two key factors have hindered the development of recombinant proteins as therapeutic agents—their generally short half-lives in the circulation and their potential antigenicity and immunogenicity. As used herein and generally in the art, the term "antigenicity" refers to the ability of a molecule to bind to preexisting antibodies, while the term "immunogenicity" refers to the ability to evoke an immune response in vivo, whether that response involves the formation of antibodies (a "humoral response") or the stimulation of cellular immune responses. For the administration of recombinant therapeutic proteins, intravenous (i.v.) administration is often desirable in order to achieve the highest circulating activities and to minimize problems of bioavailability and degradation. However, the half-lives of small proteins following i.v. administration are usually extremely short (see examples in Mordenti, J., et al., (1991) *Pharm Res* 8:1351-1359; Kuwabara, T., et al., (1995) *Pharm Res* 12:1466-1469). Healthy kidneys generally retain in the bloodstream proteins with hydrodynamic radii exceeding that of serum albumin, which has a Stokes radius of c. 36 Å and a molecular weight of c. 66,000 Daltons (66 kDa). However, smaller proteins, such as granulocyte colony-stimulating factor ("G-CSF") and ribonuclease, are cleared rapidly from the bloodstream by glomerular filtration (Brenner, B. M., et al. (1978) *Am J Physiol* 234:F455-F460; Venkatachalam, M. A., et al. (1978) *Circ Res* 43:337-347; Wilson, G., (1979) *J Gen Physiol* 74:495-509). As a result, maintenance of therapeutically useful concentrations of small recombinant proteins in the circulation is problematic following i.v. administration. Therefore, higher concentrations of such proteins and more frequent injections must be administered. The high dose rate increases the cost of therapy, decreases the likelihood of patient compliance and increases the risk of adverse events, e.g., immune reactions. Both cellular and humoral immune responses can reduce the circulating concentrations of injected recombinant proteins to an extent that may preclude the administration of an effective dose or may lead to treatment-limiting events such as anaphylaxis (Pui, C.-H., et al. (2001) *J Clin Oncol* 19:697-704).

Alternative routes of administration, such as subcutaneous (s.c.) or intramuscular (i.m.) injections, can overcome some of these problems, by providing more gradual release of recombinant proteins into the circulation. However, the bioavailability can be quite low, making it difficult to achieve effective circulating concentrations of such drugs. A further problem that may be related to the poor bioavailability of drugs administered s.c. or i.m. is the increased probability of degradation of the therapeutic protein at the site of injection.

Modification of recombinant proteins by the covalent attachment of derivatives of poly(ethylene glycol) ("PEG") has been investigated extensively as a means of addressing the shortcomings discussed above (reviewed in Sherman, M. R., et al. (1997) in: *Poly(ethylene glycol): Chemistry and Biological Applications*, Harris, J. M., et al., eds., American Chemical Society, Washington, D.C., pp. 155-169; Roberts, M. J., et al. (2002) *Adv Drug Deliv Res* 54:459-476). The attachment of PEG derivatives to proteins has been shown to stabilize the proteins, improve their bioavailability and/or reduce their immunogenicity in vivo. (The covalent attachment of PEG derivatives to a protein or other substrate is referred to herein, and is known in the art, as "PEGylation.") In addition, PEGylation can increase the hydrodynamic radius of proteins significantly. When a small protein, such as a cytokine or polypeptide hormone, is coupled to a single long strand of PEG (e.g., having a molecular weight of at least about 18 kDa), the resultant conjugate has a larger hydrodynamic radius than that of serum albumin and its clearance via the renal glomeruli is dramatically retarded. The combined effects of PEGylation—reduced proteolysis, reduced immune recognition and reduced rates of renal clearance—confer substantial advantages on PEGylated proteins as therapeutic agents.

Since the 1970s, attempts have been made to use the covalent attachment of polymers to improve the safety and efficacy of various proteins for pharmaceutical use (see, e.g., U.S. Pat. No. 4,179,337). Some examples include the coupling of PEG or poly(ethylene oxide) (PEO) to adenosine deaminase (EC 3.5.4.4) for use in the treatment of severe combined immunodeficiency disease (Davis, S., et al. (1981) *Clin Exp Immunol* 46:649-652; Hershfield, M. S., et al. (1987) *N Engl J Med* 316:589-596). Other examples include the coupling of PEG to superoxide dismutase (EC 1.15.1.1) for the treatment of inflammatory conditions (Saifer, M., et al., U.S. Pat. Nos. 5,006,333 and 5,080,891) and to urate oxidase (EC 1.7.3.3) for the elimination of excess uric acid from the blood and urine (Inada, Y., Japanese Patent Application 55-099189; Kelly, S. J., et al. (2001) *J Am Soc Nephrol* 12:1001-1009; Williams, L. D., et al., PCT publication WO 00/07629 A3, corresponding to U.S. Pat. No. 6,576,235; Sherman, M. R., et al., PCT publication WO 01/59078 A2).

PEOs and PEGs are polymers composed of covalently linked ethylene oxide units. These polymers have the following general structure:

$$R_1-(OCH_2CH_2)_n-R_2$$

where $R_2$ may be a hydroxyl group (or a reactive derivative thereof) and $R_1$ may be hydrogen, as in "PEG diol", a methyl group, as in monomethoxyPEG ("mPEG"), or another lower alkyl group, e.g., as in iso-propoxyPEG or t-butoxyPEG. The parameter n in the general structure of PEG indicates the number of ethylene oxide units in the polymer and is referred to herein and in the art as the "degree of polymerization." PEGs and PEOs can be linear, branched (Fuke, I., et al. (1994) *J Control Release* 30:27-34) or star-shaped (Merrill, E. W.

(1993) *J Biomater Sci Polym Ed* 5:1-11). PEGs and PEOs are amphipathic, i.e. they are soluble in water and in certain organic solvents and they can adhere to lipid-containing materials, including enveloped viruses and the membranes of animal and bacterial cells. Certain random or block or alternating copolymers of ethylene oxide ($OCH_2CH_2$) and propylene oxide, which has the following structure:

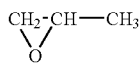

have properties that are sufficiently similar to those of PEG that these copolymers are thought to be suitable replacements for PEG in certain applications (see, e.g., U.S. Pat. Nos. 4,609,546 and 5,283,317). The term "polyalkylene oxides" and the abbreviation "PAOs" are used herein to refer to such copolymers, as well as to PEG or PEO and poly(oxyethylene-oxymethylene) copolymers (U.S. Pat. No. 5,476,653). As used herein, the term "polyalkylene glycols" and the abbreviation "PAGs" are used to refer generically to polymers suitable for use in the conjugates of the invention, particularly PEGs, more particularly PEGs containing a single reactive group ("mono functionally activated PEGs").

Commonly, several (e.g., 5 to 10) strands of one or more PAGs, e.g., one or more mPEGs with a molecular weight of about 5 kDa to about 10 kDa, are coupled to the target protein via primary amino groups (the epsilon amino groups of lysine residues and the alpha amino group of the N-terminal amino acid). More recently, conjugates have been synthesized containing a single strand of mPEG of higher molecular weight, e.g., 12 kDa, 20 kDa or 30 kDa. Direct correlations have been demonstrated between the plasma half-lives of the conjugates and an increasing molecular weight and/or increasing number of strands of PEG coupled (Clark, R., et al. (1996) *J Biol Chem* 271:21969-21977). On the other hand, as the number of strands of PEG is increased, so is the probability that an amino group in an essential region of the bioactive component (particularly if the bioactive component is a protein) will be modified, impairing its biological function (e.g., catalysis by an enzyme or receptor binding by a cytokine). For larger proteins that contain many amino groups, and for enzymes with substrates of low molecular weight, this tradeoff between increased duration of action and decreased specific activity may be acceptable, since it produces a net increase in the biological activity of the PEG-containing conjugates in vivo. For smaller proteins, such as polypeptide hormones and cytokines, however, a relatively high degree of substitution is likely to decrease the functional activity to the point of negating the advantage of an extended half-life in the bloodstream (Clark, R., et al., supra).

Certain of the present inventors have pioneered a variety of PEGylation strategies and have applied them to several proteins to achieve the desirable combination of favorable pharmacokinetics and increased potency in vivo. These proteins include granulocyte-macrophage colony-stimulating factor ("GM-CSF") (Saifer, M. G. P., et al. (1997) *Polym Preprints* 38:576-577; Sherman, M. R., et al. (1997) supra) and recombinant mammalian uricase (see PCT publications WO 00/07629 and WO 01/59078; Kelly, S. J., et al., supra; U.S. Pat. No. 6,576,235). Using GM-CSF as a model cytokine, certain of the present inventors demonstrated that the attachment of one or two strands of MPEG of high molecular weight (about 36 kDa) was sufficient to enhance dramatically the potency of recombinant murine GM-CSF in vivo (Saifer, M. G. P., et al. (1997) supra; Sherman, M. R., et al. (1997) supra). Studies have also been conducted in which recombinant mammalian urate oxidase (uricase) was modified and explored as a potential treatment for intractable gout (see PCT publications WO 00/07629, corresponding to U.S. Pat. No. 6,576,235, and WO 01/59078, the disclosures of which are entirely incorporated herein by reference). When the PEG-uricase was used to treat uricase-deficient mice (uox −/−) that displayed profound uric acid-induced nephropathy, it was found to be well tolerated, effective and substantially non-immunogenic. Treated mice exhibited improved renal function for the duration of treatment (10 weeks) and had substantially less uric acid-related kidney damage than untreated uox −/− mice, as demonstrated by microscopic magnetic resonance imaging (Kelly, S. J., et al. (2001) supra).

The covalent attachment of strands of a PAG to a polypeptide molecule is disclosed in U.S. Pat. No. 4,179,337 to Davis, F. F., et al., as well as in Abuchowski, A., et al. (1981) in: *Enzymes as Drugs*, Holcenberg, J. S., et al., eds., John Wiley and Sons, New York, pp. 367-383. These references disclose that enzymes and other proteins modified with mPEGs have reduced immunogenicity and antigenicity and have longer lifetimes in the bloodstream, compared to the corresponding unmodified proteins. The resultant beneficial properties of the chemically modified conjugates are very useful in a variety of therapeutic applications.

To effect the covalent attachment of PEG or polyalkylene oxides to a protein, at least one of the hydroxyl end groups of the polymer must first be converted into a reactive functional group. This process is frequently referred to as "activation" and the product is called "activated PEG" or activated polyalkylene oxide. MonomethoxyPEG that is capped on one end with an unreactive, chemically stable methyl ether (the "methoxyl group") and on the other end with a functional group reactive towards amino groups on a protein molecule is most commonly used for such approaches. So-called "branched" mPEGs, which contain two or more methoxyl groups distal from a single activated functional group, are used less commonly. An example is di-mPEG-lysine, in which the carboxyl group of lysine is most often activated by esterification with N-hydroxysuccinimide (Harris, J. M., et al., U.S. Pat. No. 5,932,462).

The activated polymers are reacted with a therapeutic agent having nucleophilic functional groups that serve as attachment sites. One nucleophilic functional group commonly used as an attachment site is the epsilon amino group of lysine residues. Free carboxylic acid groups, suitably activated carbonyl groups, oxidized carbohydrate moieties and thiol groups have also been used as attachment sites.

The hydroxyl group of MPEG has been activated with cyanuric chloride and the resulting compound then coupled with proteins (Abuchowski, A., et al. (1977) *J Biol Chem* 252:3582-3586; Abuchowski, A., et al. (1981) supra). The use of this method has disadvantages however, such as the toxicity of cyanuric chloride and its non-specific reactivity for proteins having functional groups other than amines, such as solvent-accessible cysteine or tyrosine residues that may be essential for function.

In order to overcome these and other disadvantages, alternative activated PEGs have been introduced, such as succinimidyl succinate derivatives of mPEG ("SS-PEG") (Abuchowski, A., et al. (1984) *Cancer Biochem Biophys* 7:175-186). Under mild conditions, SS-PEG reacts quickly with proteins (within 30 minutes), yielding active, yet extensively modified conjugates.

M. Saifer, et al., in U.S. Pat. No. 5,468,478, disclose polyalkylene glycol-mono-N-succinimidyl carbonates and conjugates produced therefrom. S. Zalipsky, in U.S. Pat. No. 5,612, 460, discloses methods for preparation of poly(ethylene glycol)-N-succinimidyl carbonates. This form of the polymer ("SC-PEG") reacts readily with the amino groups of proteins, as well as peptides of low molecular weight and other materials that contain free amino groups, with which it forms urethane bonds.

Urethane (or carbamate) linkages between the amino groups of the protein and the PEG are also known in the art to be produced from other PEG-carbonate derivatives (Beauchamp, C., et al. (1983) *Anal Biochem* 131:25-33; Veronese, F. M., et al. (1985) *Appl Biochem Biotechnol* 11:141-152). Reactive MPEG intermediates and methods for their use are also known in the art for the synthesis of PEG conjugates of bioactive components linked via amide bonds, ester bonds, secondary amines and thioester bonds, among others.

T. Suzuki et al. ((1984) *Biochim Biophys Acta* 788:248-255) covalently coupled immunoglobulin G ("IgG") to mPEG that had been activated by cyanuric chloride. They studied the biological and physicochemical properties, such as antigen-binding activity and the molecular structure, size-exclusion chromatographic behavior, surface activity, interfacial aggregability and heat aggregability that induced nonspecific activation of complement by the PEG-IgG conjugates. The coupling of PEG to IgG increased the apparent Stokes radius and the surface activity of IgG and stabilized IgG to heating and/or the exposure to interfaces, while no structural denaturation of IgG was observed. The suppression of nonspecific aggregability was attributed mainly to the steric inhibition of the association between the PEGylated IgG molecules. These results indicated the utility of mPEG-coupled IgG as an intravenous preparation and also suggested the utility of PEG as an additive to stabilize unmodified IgG for intravenous use.

K. A. Sharp et al. ((1986) *Anal Biochem* 154:110-117) investigated the possibility of producing biospecific affinity ligands for separating cells in aqueous two-phase polymer systems on the basis of cell surface antigens. Rabbit anti-human erythrocyte IgG was reacted with cyanuric chloride-activated mPEGs with molecular weights of approximately 0.2, 1.9 and 5 kDa at various molar ratios of PEG to lysine groups on the protein. The partition coefficient of the protein in a two-phase system containing dextran and PEG increased with increasing degree of modification and increasing molecular weight of the MPEG. There was a concomitant loss in ability to agglutinate human erythrocytes.

R. H. Tullis, in U.S. Pat. No. 4,904,582, discloses oligonucleotide conjugates wherein the oligonucleotides are joined through a linking arm to a hydrophobic moiety, which could be a polyoxyalkylene group. The resulting conjugates are said to be more efficient in membrane transport, so as to be capable of crossing the membrane and effectively modulating a transcriptional system. In this way, the compositions can be used in vitro and in vivo for studying cellular processes, protecting mammalian hosts from pathogens, facilitating gene therapy, and the like.

Excessive conjugation of polymers and/or conjugation involving the active site of a therapeutic moiety where groups associated with bioactivity are found, however, can often result in loss of activity and, thus, in loss of therapeutic efficacy. This is often the case with lower molecular weight peptides that have few attachment sites that are not associated with bioactivity. For example, I. Benhar et al. ((1994) *Bioconjug Chem* 5:321-326) observed that PEGylation of a recombinant single-chain immunotoxin resulted in the loss of specific target immunoreactivity of the immunotoxin. The loss of activity of the immunotoxin was the result of attachment of PEG to two lysine residues within the antigen-combining region of the immunotoxin.

Although the covalent attachment of PAGs and PAOs (e.g., PEGs, PEOs, etc.) to therapeutic proteins is intended to eliminate their immunoreactivity, PEGylated proteins remain weakly immunogenic. This immunogenicity appears to be due, at least in part, to the fact that PEG and PAO polymers are themselves somewhat antigenic and immunogenic. For example, rabbits have been immunized to various PEGs by injecting the animals with conjugates in which PEG was coupled to an immunogenic carrier protein (Richter, A. W., et al. (1983) *Int Arch Allergy Appl Immunol* 70:124-131). In addition, a monoclonal antibody that reacts with the polyether backbone of PEG has been developed by injecting mice with an mPEG conjugate of β-glucuronidase and selecting a hybridoma clone that secretes an anti-PEG antibody (Cheng, T.-L., et al. (1999), *Bioconjug. Chem.* 10:520-528; Cheng, T.-L., et al. (2000), *Bioconjug. Chem.* 11:258-266; Tsai, N.-M., et al. (2001), *Biotechniques* 30:396-402; Roffler, S., et al., U.S. Pat. Nos. 6,596,849 and 6,617,118; the disclosures of all of which are incorporated herein by reference in their entireties). Another monoclonal antibody that reacts with the polyether backbone of PEG has been disclosed recently by Roberts, M. J., et al., in U.S. Patent Application No. 2003/001704 A1.

A number of investigators have disclosed the preparation of linear or branched "non-antigenic" PEG polymers and derivatives or conjugates thereof (see, e.g., U.S. Pat. Nos. 5,428,128; 5,621,039; 5,622,986; 5,643,575; 5,728,560; 5,730,990; 5,738,846; 5,811,076; 5,824,701; 5,840,900; 5,880,131; 5,900,402; 5,902,588; 5,919,455; 5,951,974; 5,965,119; 5,965,566; 5,969,040; 5,981,709; 6,011,042; 6,042,822; 6,113,906; 6,127,355; 6,132,713; 6,177,087, and 6,180,095; see also PCT publication WO 95/13090 and published U.S. patent application nos. 2002/0052443, 2002/0061307 and 2002/0098192). Most of the examples in the foregoing patents and patent applications employ polymers containing one or more strands of mPEG, e.g., di-mPEG-lysine. To date, however, there has been no disclosure of a mechanism for rendering the PEG in such polymers or conjugates non-antigenic.

Thus, there exists a need for the identification of methods of producing PAO-containing (e.g., PEG- and/or PEO-containing) conjugates, particularly conjugates between such water-soluble polymers and therapeutic proteins, with reduced, substantially reduced or no detectable antigenicity. Such conjugates will have the benefits provided by the polymer component of increased stability and bioavailability in vivo, but will not elicit a substantial immune response in an animal into which the conjugates have been introduced for therapeutic or diagnostic purposes.

BRIEF SUMMARY OF THE INVENTION

The present invention addresses the needs identified above, and provides methods for the preparation of conjugates of water-soluble polymers (e.g., poly(ethylene glycol) and derivatives thereof) and bioactive components, particularly therapeutic bioactive components, such as proteins. The invention also provides polymers and conjugates produced by such methods, which polymers and conjugates have reduced antigenicity and immunogenicity, compared to alkoxyl-containing polymers and conjugates of the same bioactive component prepared with alkoxyPEGs, e.g., MPEG. The invention also provides compositions comprising such conjugates, kits containing such conjugates and compositions and methods of use of the conjugates and compositions in a variety of therapeutic and diagnostic regimens.

In one aspect, the invention provides a conjugate comprising one or more bioactive components covalently linked to at least one linear or branched monofunctionally activated polyalkylene glycol, wherein the monofunctionally activated polyalkylene glycol does not comprise a methoxyl group, another alkoxyl group or an aryloxyl group at any terminus. In certain such embodiments, the conjugate has reduced or substantially reduced antigenicity compared to a conjugate prepared using an alkoxypoly(ethylene glycol), e.g., MPEG, or a branched polymer containing MPEG, such as di-mPEG-lysine.

Polyalkylene glycols that are particularly suitable for use in the synthesis of the conjugates of the invention include, but are not limited to, poly(ethylene glycols) and copolymers of ethylene oxide and propylene oxide; particularly preferred are PEGs, and more particularly preferred are monofunctionally activated PEGs (e.g., PEGs that are activated at a single terminus, including hydroxyPEG-monoaldehydes, hydroxyPEG-monovinyl-sulfones, reactive esters of hydroxyPEG-monocarboxylic acids and hydroxyPEG-monophenyl carbonate derivatives). Other intermediates that can be useful for the synthesis of the reactive polymer derivatives include other hydroxyPEG-monoacids and hydroxyPEG-monoacetals.

In certain such embodiments, the polyalkylene glycol has a molecular weight of from about 1,000 Daltons to about 100 kDa, preferably about 2 kDa to about 60 kDa; about 2 kDa to about 30 kDa, about 5 kDa to about 20 kDa; about 10 kDa to about 30 kDa; about 10 kDa to about 20 kDa; two branches each with a molecular weight of about 2 kDa to about 30 kDa; and more preferably two branches, each of about 18 kDa to about 22 kDa. Conjugates according to this aspect of the invention may comprise one or more strands of polyalkylene glycol, in certain embodiments preferably from about one to about 10 strands, from about one to about five strands, more preferably from about one to about three strands, and most preferably from about one to about two strands; in other embodiments preferably from about five to about 100 strands, from about 10 to about 50 strands and more preferably from about six to about 20 strands per subunit of high molecular weight enzyme proteins. In a particularly preferred such embodiment, the polyalkylene glycol used in the conjugate comprises one or two strands of a monofunctionally activated poly(ethylene glycol) (e.g., a reactive ester of a hydroxyPEG-monoacid, a hydroxyPEG-monoaldehyde, a hydroxyPEG-monovinylsulfone or a hydroxyPEG-monophenyl carbonate derivative) having a molecular weight of from about 18 kDa to about 22 kDa or about 27 kDa to about 33 kDa.

Suitable bioactive components for use in the conjugates or compositions of the invention include, but are not limited to, a variety of peptides, proteins, glycoproteins, organic compounds, amine-containing compounds, carboxyl-containing compounds, hydroxyl-containing compounds and thiol-containing compounds.

The invention also provides methods of producing conjugates between a bioactive compound and a monofunctionally activated polyalkylene glycol, for example comprising: (a) obtaining or preparing a linear or branched polyalkylene glycol comprising at least one unreactive blocking group that can be subsequently removed, such as one or more triphenylmethyl groups ("trityl groups"); (b) producing a derivative of the polyalkylene glycol by reacting it with at least one derivatizing compound under conditions such that the polyalkylene glycol is derivatized with one derivatizing group (such as one carboxyl group) at an end that lacks the blocking group(s); (c) removing the blocking group(s) without removing the derivatizing group to produce, in one or more steps, a monofunctionally activated polyalkylene glycol; and (d) contacting the monofunctionally activated polyalkylene glycol with at least one bioactive component under conditions that favor the covalent binding of the bioactive component to the monofunctionally activated polyalkylene glycol. Preferably, the conjugates produced by such methods are of reduced, substantially reduced or undetectable antigenicity and immunogenicity, when compared to conjugates derivatized to the same extent with mPEG of similar size, structure and linkage to the bioactive agent. The invention also provides conjugates produced by such methods.

The invention also provides pharmaceutical or veterinary compositions comprising the conjugates of the invention and at least one excipient or carrier that is acceptable for pharmaceutical or veterinary use.

In additional embodiments, the invention also provides methods of preventing, diagnosing or treating physical disorders in animals (such as mammals, including humans) using the conjugates or compositions of the invention. One such method comprises, for example, administering to an animal suffering from or predisposed to a physical disorder (such as anemia, arthritis, cancers, Alzheimer's disease, enzymatic deficiencies, cardiovascular disease, hypertension, infectious diseases, metabolic diseases, neurologic diseases, neutropenia, hyperuricemia and manifestations thereof (e.g., gout), genetic deficiency diseases or disorders, and the like) an effective amount of one or more of the conjugates or compositions of the invention, which may be administered to the animal, especially mammals and most especially humans, orally, topically or parenterally, for example intravenously, intramuscularly or subcutaneously.

In additional embodiments, the invention provides compositions comprising one or more of the conjugates of reduced antigenicity of the invention that may further comprise one or more additional components or reagents, such as one or more buffer salts, one or more carbohydrate excipients, one or more carrier proteins, one or more enzymes, one or more detergents, one or more nucleic acid molecules, one or more polymers such as PEG, and the like. The invention also provides kits comprising the conjugates of reduced antigenicity and/or compositions of the invention.

In additional embodiments, the invention provides PEG-liposomes of reduced immunoreactivity prepared using monofunctionally activated polyalkylene glycols that lack methoxyl or other alkoxyl groups, rather than monofunctionally activated mPEG. Other preferred embodiments of the present invention will be apparent to one of ordinary skill in light of the following drawings and description of the invention, and of the claims.

BRIEF DESCRIPTION OF THE DRAWINGS

FIG. 6a shows data from the second bleeding of rabbits that had received four injections of PEG-uricase in incomplete Freund's adjuvant. FIG. 6b shows data from the third bleeding of the same rabbits after they had received five injections of PEG-uricase in incomplete Freund's adjuvant.

DETAILED DESCRIPTION OF THE INVENTION

Figure 1:
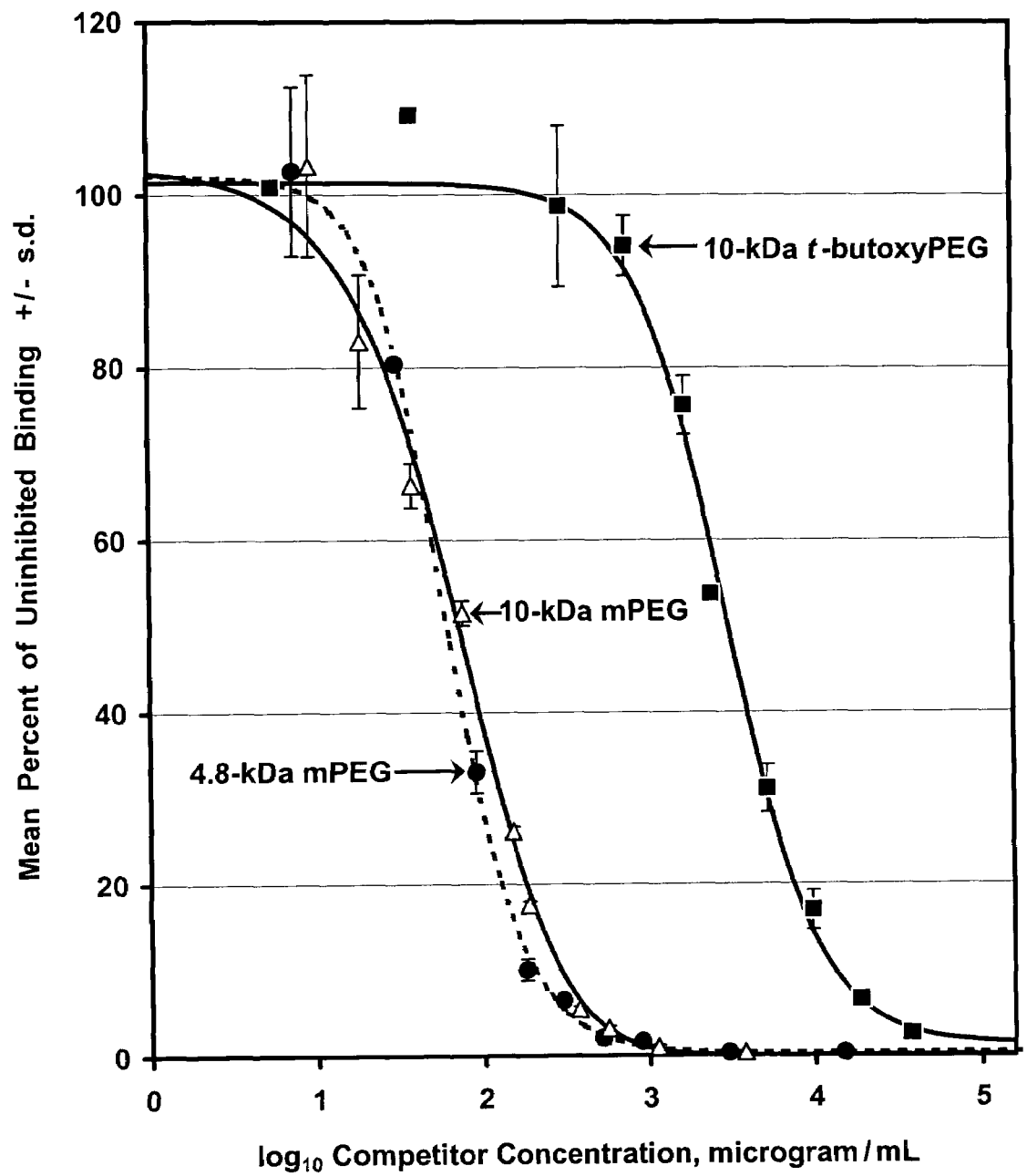
FIG. 1 displays the results from a competitive enzyme-linked immunosorbent assay ("ELISA") analysis. In this assay, an mPEG conjugate of one protein was bound to the 96-well assay plate, and the inhibition of binding of rabbit antibodies to an mPEG conjugate of another protein by solutions of MPEG or t-butoxyPEG was measured.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are described hereinafter.

Definitions

About: As used herein when referring to any numerical value, the term "about" means a value of ±10% of the stated value (e.g., "about 50° C." encompasses a range of temperatures from 45° C. to 55° C., inclusive; similarly, "about 100 mM" encompasses a range of concentrations from 90 mM to 110 mM inclusive).

Bioactive Component: As used herein, the term "bioactive component" refers to a compound, molecule, moiety or complex that has a particular biological activity in vivo, in vitro or ex vivo upon a cell, tissue, organ or organism, and that is capable of being bound to one or more polyalkylene glycols to form the conjugates of the invention. Preferred bioactive components are described in detail below.

Bound: As used herein, the term "bound" refers to binding or attachment that may be covalent, e.g., by chemically coupling, or non-covalent, e.g., ionic interactions, hydrophobic interactions, hydrogen bonds, etc. Covalent bonds can be, for example, ester, ether, phosphoester, thioester, thioether, urethane, amide, peptide, imide, carbon-sulfur bonds, carbon-phosphorus bonds, and the like. The term "bound" is broader than and includes terms such as "coupled," "linked" and "attached."

Coupled: The term "coupled", as used herein, refers to attachment by covalent bonds or by strong non-covalent interactions, typically and preferably to attachment by covalent bonds. Any method normally used by those skilled in the art for the coupling of biologically active materials can be used in the present invention.

Disease, disorder, condition: As used herein, the terms "disease" or "disorder" refer to any adverse condition of a human or animal including tumors, cancers, allergies, addiction, autoimmunity, poisoning or impairment of optimal mental or bodily function. "Conditions" as used herein includes diseases and disorders but also refers to physiologic states. For example, fertility is a physiologic state but not a disease or disorder. Compositions of the invention suitable for preventing pregnancy by decreasing fertility would therefore be described as a treatment of a condition (fertility), but not a treatment of a disorder or disease. Other conditions are understood by those of ordinary skill in the art.

Effective Amount: As used herein, the term "effective amount" refers to an amount of a given conjugate or composition that is necessary or sufficient to realize a desired biologic effect. An effective amount of a given conjugate or composition of the present invention would be the amount that achieves this selected result, and such an amount could be determined as a matter of routine by a person skilled in the art. For example, an effective amount for treating an immune system deficiency could be that amount necessary to cause activation of the immune system, resulting in the development of an antigen-specific immune response upon exposure to an antigen. The term is also synonymous with "sufficient amount." The effective amount for any particular application can vary depending on such factors as the disease or condition being treated, the particular composition being administered, the size of the subject, and/or the severity of the disease or condition. One of ordinary skill in the art can determine empirically the effective amount of a particular conjugate or composition of the present invention without necessitating undue experimentation.

Immune response: As used herein, the term "immune response" refers to a humoral immune response (i.e., the formation of antibodies) and/or a cellular immune response leading to the activation or proliferation of B and/or T-lymphocytes and/or antigen-presenting cells. In some instances, however, the immune responses may be of low intensity and become detectable only when using at least one substance in accordance with the invention. "Immunogenic" refers to an agent that is capable of stimulating the immune system of a living organism, so that one or more functions of the immune system are increased and directed towards the immunogenic agent.

One, a, or an: When the terms "one," "a," or "an" are used in this disclosure, they mean "at least one" or "one or more," unless otherwise indicated.

Polypeptide: As used herein, the term "polypeptide" refers to a molecule composed of monomers (amino acids) linearly linked by amide bonds (also known as peptide bonds). It indicates a molecular chain of amino acids and does not refer to a specific length of the product. Thus, dipeptides, tripeptides, oligopeptides, peptides of unspecified length and proteins are included within the definition of polypeptide. This term is also intended to refer to the products of post-expression modifications of the polypeptide, for example, glycosylation, acetylation, phosphorylation and the like. A polypeptide may be recombinant or derived from a natural biological source, but is not necessarily translated from a designated nucleic acid sequence. It may be generated in any manner, including by chemical synthesis.

Protein and glycoprotein: As used herein, the term protein refers to a polypeptide generally of a size of above about 5 or more, 10 or more, 20 or more, 25 or more, 50 or more, 75 or more, 100 or more, 200 or more, 500 or more, 1,000 or more or 2,000 or more amino acids. Proteins generally have a defined three-dimensional structure, although they do not necessarily need to, and are often referred to as folded, as opposed to peptides and polypeptides, which often do not possess a defined three-dimensional structure, but rather can adopt a large number of different conformations, and are referred to as unfolded. Peptides may, however, also have a defined three-dimensional structure. As used herein, the term glycoprotein refers to a protein containing at least one sugar moiety attached to the protein via an oxygen-containing or a nitrogen-containing side chain of an amino acid, e.g., serine or asparagine.

Purified: As used herein, when the term "purified" is used in reference to a molecule, it means that the concentration of the molecule being purified has been increased relative to molecules associated with it in its natural environment, or the environment in which it was produced, found or synthesized. Naturally associated molecules include proteins, nucleic acids, lipids and sugars, but generally do not include water, buffers, and reagents added to maintain the integrity or facilitate the purification of the molecule being purified. For example, even if a given protein in a crude extract is diluted with an aqueous solvent during column chromatography, protein molecules are considered to be purified by this chromatography if naturally associated nucleic acids, non-desired proteins and other biological molecules are separated from the subject protein molecules. According to this definition, a substance may be 5% or more, 10% or more, 20% or more, 30% or more, 40% or more, 50% or more, 60% or more, 70% or more, 80% or more, 90% or more, 95% or more, 98% or more, 99% or more, or 100% pure when considered relative to its contaminants.

Residue: As used herein, the term "residue" refers to a specific amino acid, usually dehydrated as a result of its involvement in one or more peptide bonds, in a polypeptide backbone or side chain.

Treatment: As used herein, the terms "treatment," "treat," "treated" or "treating" refer to prophylaxis and/or therapy. When used with respect to an infectious disease, for example, the term may refer to a prophylactic treatment that increases the resistance of a subject to infection with a pathogen or, in other words, decreases the likelihood that the subject will become infected with the pathogen or will show signs of illness attributable to the infection, as well as a treatment after the subject has become infected in order to fight the infection, e.g., to reduce or eliminate the infection or to prevent it from becoming worse.

Overview

A number of previous investigators have disclosed the preparation of linear or branched non-antigenic PEG polymers or conjugates thereof (see, e.g., U.S. Pat. Nos. 5,428,128; 5,621,039; 5,622,986; 5,643,575; 5,728,560; 5,730,990; 5,738,846; 5,811,076; 5,824,701; 5,840,900; 5,880,131; 5,900,402; 5,902,588; 5,919,455; 5,951,974; 5,965,119; 5,965,566; 5,969,040; 5,981,709; 6,011,042; 6,042,822; 6,113,906; 6,127,355; 6,132,713; 6,177,087, and 6,180,095; see also PCT publication WO 95/13090 and published U.S. patent application Nos. 2002/0052443, 2002/0061307 and 2002/0098192; the disclosures of all of which are incorporated herein by reference in their entireties). However, the PEG and the conjugates in these previous reports remain at least weakly immunogenic, which can lead to the undesirable consequence of the development of antibodies to the PEG component of the conjugates when the conjugates are introduced into an animal for prophylactic, diagnostic or therapeutic purposes. Such antibodies may lead to a rapid clearing of PEG-containing bioactive conjugates, thereby reducing the bioavailability of the therapeutic compositions (Cheng, T.-L., et al. (1999), supra), as well as possibly inducing an immune-complex mediated disorder. Moreover, as yet there has been no disclosure of a mechanism for rendering the claimed PEGs or conjugates thereof substantially non-antigenic or non-immunogenic.

The present invention has overcome these limitations in the art. In general, the invention provides stable compositions and methods useful in the prevention, diagnosis and treatment of a variety of physical disorders. More particularly, the invention provides methods for producing reactive polymers of reduced antigenicity and stabilized polymer conjugates of proteins, particularly therapeutic proteins, which have reduced or substantially reduced antigenicity or which have undetectable antigenicity. In other embodiments, the invention provides conjugates produced by these methods of the invention, and compositions, particularly pharmaceutical compositions, comprising such conjugates. In additional embodiments, the invention provides methods of use of such conjugates and compositions in preventing, diagnosing and treating a variety of physical disorders. The invention also provides kits comprising one or more of the conjugates and/or compositions of the invention.

Preparation of Conjugates of Reduced Antigenicity

In one aspect, the present invention provides methods for preparing conjugates of reduced antigenicity, substantially reduced antigenicity, or undetectable antigenicity, by the covalent attachment of water-soluble polymers to one or more bioactive compounds or components, such as one or more proteins and particularly one or more therapeutic proteins. In such conjugates, the polymers chosen will themselves be of reduced antigenicity, substantially reduced antigenicity or undetectable antigenicity, compared to standard polymers typically used for preparing protein-polymer conjugates. As used herein, the term "reduced antigenicity" refers to a polymer (e.g., a PAO or PAG, particularly a PEG, and most particularly a monofunctionally activated PEG), or a conjugate or composition comprising or synthesized using such a polymer, wherein the ability of the polymer to react with antibodies formed against more antigenic polymers (e.g., mPEG) has been reduced by any amount. Preferably, the antigenicity is reduced by at least about 30%, more preferably reduced by at least about 50%, and most preferably reduced by more than about 75% compared to the more antigenic polymer. By extension, then, a polymer (or conjugate or composition comprising or synthesized using such a polymer) is said to be of "substantially reduced antigenicity" if the polymer (or conjugate or composition) has about or less than 20%, more preferably about or less than 15%, still more preferably about or less than 10%, and most preferably about or less than 1%, of the antigenicity of the corresponding antigenic polymer (e.g., mPEG). Finally, a polymer (or conjugate or composition comprising or synthesized using such a polymer) is said to have "no detectable antigenicity" if the polymer, conjugate or composition has no detectable antigenicity when assayed with art-known methods (e.g., ELISA or other methods of detecting antigenicity, such as those known in the art and as described in the Examples herein).

Polymers

Polyalkylene glycols that are particularly suitable for use in preparing the conjugates of the invention include, but are not limited to, poly(ethylene glycols), and copolymers of ethylene oxide and propylene oxide; particularly preferred are PEGs, and more particularly preferred are monofunctionally activated hydroxyPEGs (e.g., hydroxyPEGs activated at a single terminus, including reactive esters of hydroxyPEG-monocarboxylic acids, hydroxyPEG-monoaldehydes, hydroxyPEG-monoamines, hydroxyPEG-monohydrazides, hydroxyPEG-monocarbazates, hydroxyPEG-monoiodoacetamides, hydroxyPEG-monomaleimides, hydroxyPEG-monoorthopyridyl disulfides, hydroxyPEG-monooximes, hydroxyPEG-monophenyl carbonates, hydroxyPEG-monophenyl glyoxals, hydroxyPEG-monothiazolidine-2-thiones, hydroxyPEG-monothioesters, hydroxyPEG-monothiols, hydroxyPEG-monotriazines and hydroxyPEG-monovinylsulfones).

Particularly preferred polymers for use in preparing the conjugates of the present invention, which have reduced antigenicity, substantially reduced antigenicity, or no detectable antigenicity, are monofunctionally activated PEGs that do not contain methoxyl groups, other alkoxyl groups or aryloxyl groups. The substitution of such monofunctionally activated PEGs in place of monofunctionally activated mPEG in the synthesis of conjugates of the invention confers on the resulting conjugates an unexpectedly decreased antigenicity, i.e., a decreased ability to interact with antibodies developed against mPEG conjugates of the same bioactive component. The resultant conjugates also have decreased immunogenicity, i.e., decreased ability to evoke an immune response.

In one aspect of the invention, monofunctionally activated PEGs can be synthesized by using suitable reversibly blocked derivatives of the activating group as an initiator for polymerization of ethylene oxide (Akiyama, Y., et al. (2000) *Bioconjug Chem*, 11:947-950). Akiyama et al. provide conditions for the synthesis of a monohydroxyl, monoacetal derivative of PEG by using potassium 3,3-diethoxypropanolate as the initiator for polymerization of ethylene oxide. Since Akiyama et al. did not recognize the most desirably reduced antigenicity or immunogenicity of this intermediate, they proceeded to convert the terminal hydroxyl group to a thiol by terminating the polymerization by the addition of methanesulfonyl chloride, thereby producing a heterobifunctional PEG, instead of a PEG derivative of this invention. As further evidence that this group of workers did not recognize the utility of a hydroxyl terminated monofunctionally activated PEG, they have published and patented methods for synthesis of alternative heterobifunctional PEGs from monohydroxyl, monofunctionally activated PEGs and in some cases have even "end-capped" the hydroxyPEGs with methoxyl groups. Similarly, Bentley, M. D., et al., in published U.S. Patent Application No. 2002/0072573 A1, disclose polymer compositions and methods that reflect no recognition of the immunologic advantage of hydroxyl-terminated monofunctionally activated polymers and teach the desirability of converting the terminal hydroxyl groups of such polymers to methoxyl groups.

In an alternative aspect of the present invention, monofunctionally activated PEGs can be synthesized by controlling the extent of activation of linear PEGs containing hydroxyl groups at both ends ("PEG diols") in order to limit the amount of bis-activated PEG to an acceptably low level, e.g., <5%, preferably <2% or more preferably <1%, as an alternative to the method shown in Example 5. In a particularly preferred aspect, monofunctionally activated PEGs can be synthesized from monofunctional PEGs from which an unreactive blocking group can be removed following the derivatization of the PEG, without removing the derivatizing group. An example of a derivatized PEG is a PEG-carboxylic acid and examples of unreactive blocking groups that can be removed following derivatization are aryloxyl groups (Bentley, M. D., et al., PCT publication WO 01/26692 A1), trityl groups (Kocienski, P. J., (1994) *Protecting Groups*, Georg Thieme Verlag, Stuttgart, pp. 54-58), and t-butoxyl groups. The t-butoxyPEG-carboxylic acid can be activated, e.g., with N-hydroxysuccinimide. Finally, the t-butoxyl group can be removed by anhydrous acidolysis to produce an activated PEG carboxylic acid derivative that has a hydroxyl group, instead of a methoxyl group at the distal end of the polymer. In a more preferred embodiment, the t-butoxyPEG-carboxylic acid can be converted to hydroxyPEG-carboxylic acid by acidolysis prior to activation of the carboxyl group with N-hydroxysuccinimide. In another embodiment of this invention, t-butoxyPEG-acetals are synthesized by contacting t-butoxyPEG with a haloacetal and converting the product to a hydroxyPEG-acetal or hydroxyPEG-aldehyde by selective anhydrous acidolysis to remove the t-butoxyl group. The acetal may be converted to an aldehyde (or an aldehyde hydrate) in preparation for its coupling to an amine-containing compound by reductive alkylation (Bentley, M. D., et al., U.S. Pat. No. 5,990,237). In another embodiment, an aryloxyl protecting group that is distal from the reactive terminus of the polymer can be removed by catalytic hydrogenolysis, thereby producing a monoactivated hydroxyPAG of this invention. Alternatively, reversible blocking of all except one of the terminal hydroxyl groups, as described in Example 6, can be employed in the synthesis of monofunctionally activated hydroxyPAGs.

The PAG polymers used in preparing the conjugates of the present invention may be linear polymers, or may be branched at one or more points within the polymer molecule. In addition, the polymers used to form the conjugates of the invention may be homopolymers, in which multiple units of a single monomer type are linked together to form the polymer, such as poly(ethylene glycol) or they may be heteropolymers or copolymers (in which monomeric units of two or more structures are linked together to form the polymer, such as a copolymer of ethylene oxide and propylene oxide). Such copolymers may be random copolymers, block copolymers or alternating copolymers.

Polymers used in accordance with the invention may be unreactive polymers or reactive polymers. As used herein, "unreactive polymers" are those polymers that will not attach covalently to a protein. Examples of such "unreactive polymers" include, but are not limited to, mPEG, which is a linear polymer of ethylene oxide units with a hydroxyl group at one end and a methoxyl group at the other end, and PEG diol, which is a linear polymer of ethylene oxide units with hydroxyl groups at both ends. As used herein, "reactive polymers" are those polymers that can react with solvent-accessible nucleophilic groups, e.g., thiol groups or amino groups on a bioactive component (such as a protein), including but not limited to the alpha amino group or the epsilon amino groups of lysine residues. Examples of "reactive polymers" include, but are not limited to, PEGs in which a hydroxyl end group has been converted to or replaced by an electrophilic group, such as succinimidyl propionic acid (as in "SPA-PEG") or a p-nitrophenyl carbonate (as in "NPC-PEG"), or an aldehyde as in PEG-aldehyde. In addition to polyalkylene oxides, suitable polymers may include polyvinyl alcohols, poly(oxyethylene-oxymethylene) copolymers, polyamides (e.g., Rose, K., PCT publication WO 00/12587), polycarboxylates, poly(vinylpyrrolidones) (von Specht, B.-U., et al. (1973) *Hoppe-Seyler's Z Physiol Chem* 354:1659-1660), poly D-amino acids and/or poly L-amino acids, polyacryloyl-morpholine (Rocca, M., et al. (1996) *Int J Artif Organs* 19:730-734) and dextrans (Iakunitskaya, L. M., et al. (1980) *Prikl Biokhim Mikrobiol* 16:232-237). Derivatives of PEGs, PEOs and other PAOs that react more or less selectively with various sites on the target bioactive components are well known in the art and can be purchased from suppliers such as Fluka (Milwaukee, Wis.); NOF Corporation (Tokyo, Japan); Shearwater Corporation (Huntsville, Ala.), a subsidiary of Nektar Therapeutics (San Carlos, Calif.); Sigma Chemical Company (St. Louis, Mo.) or SunBio, Inc. (Anyang City, South Korea).

Activated forms of polymers that are suitable for use in the methods and compositions of this invention can include any hydroxyl terminated, monofunctionally active forms of polymers that are known in the art. For example, linear and branched PAOs of various sizes are suitable, including those with molecular weights (excluding the mass of the activating group) in the range of about 1 kDa to about 100 kDa. Suitable ranges of molecular weights include but are not limited to about 2 kDa to about 60 kDa; about 2 kDa to about 30 kDa; about 5 kDa to about 20 kDa; about 10 kDa to about 20 kDa; and about 18 kDa to about 60 kDa, about 20 kDa or about 30 kDa. In the case of linear PEGs, the molecular weight range of about 20 kDa to about 30 kDa corresponds to a degree of polymerization (n) in the range of about 450 to about 680 monomeric units of ethylene oxide. It should be noted that the advantages of coupling a therapeutic protein to polymers having this latter relatively high range of molecular weights (i.e., >20-30 kDa) were first observed long before the immunogenicity of mPEG was recognized (Saifer, M., et al., PCT publication WO 89/01033, published Feb. 9, 1989, which is incorporated herein by reference in its entirety).

Optionally, a linear polymer can have a reactive group at one end or both ends, thereby creating a "reactive polymer." In certain embodiments of this invention, it can be desirable to use the succinimidyl ester of the monopropionic acid derivative of PEG, as disclosed in Harris, J. M., et al., U.S. Pat. No. 5,672,662, which is incorporated herein fully by reference, or other succinimide activated PEG-carboxylic acids. In certain other embodiments, it can be desirable to use either the succinimidyl carbonate derivatives of PEG ("SC-PEG"), as described in Saifer, M., et al., U.S. Pat. Nos. 5,006,333; 5,080,891; 5,283,317 and 5,468,478, or the p-nitrophenyl carbonate derivative of PEG, as disclosed in Kelly, S. J., et al. (2001) supra; PCT publication WO 00/07629 A2, supra and corresponding U.S. Pat. No. 6,576,235, and in PCT publication WO 01/59078 A2 supra. Moreover, other types of reactive groups can be used to synthesize polymer conjugates of proteins. These derivatives include, but are not limited to, aldehyde derivatives of PEGs (Royer, G. P., U.S. Pat. No. 4,002,531; Harris, J. M., et al., U.S. Pat. No. 5,252,714), amine, bromophenyl carbonate, carbonylimidazole, chlorophenyl carbonate, fluorophenyl carbonate, hydrazide, carbazate, iodoacetamide, maleimide, orthopyridyl disulfide, oxime, phenylglyoxal, thiazolidine-2-thione, thioester, thiol, triazine and vinylsulfone derivatives of PEGs.

In certain embodiments of the invention, it is desirable to minimize the formation of intramolecular and intermolecular cross-links by polymers such as PEG during the reaction in which the polymer is coupled to the bioactive component to produce the conjugates of the invention. This can be accomplished by using polymers that are activated at only one end (referred to herein as "monofunctionally activated PEGs" or "monofunctionally activated PAGs") or polymer preparations in which the percentage of bifunctionally activated polymers (referred to in the case of linear PEGs as "bis-activated PEG diols") is less than 30%, or more preferably less than 10% or most preferably less than 2% (w/w). The use of activated polymers that are predominantly monofunctional can minimize the formation of all of the following: intramolecular cross links within an individual protein molecule, "dumbbell" structures, in which one strand of polymer connects two protein molecules, and larger aggregates or gels. When activated polymers that react with amino groups are used, the theoretical maximum number of strands of polymer that can be attached to one molecule of protein corresponds to the total number of amino groups. The actual number of amino groups that are accessible on the surface of a protein under any particular conditions of polymer coupling may be smaller than the theoretical maximum.

Conjugates of the invention may comprise one or more strands of polyalkylene glycol, preferably from about one to about 100 strands, from about one to about 20 strands per subunit of therapeutic enzymes, and from about one to about three strands, and more preferably from about one to about two strands per subunit of receptor-binding cytokines, growth factors, protein hormones and colony stimulating factors. In a particularly preferred such embodiment, the polyalkylene glycol used in preparing the conjugate comprises one or two strands of poly(ethylene glycol) (particularly a carboxyPEG, an hydroxyPEG, a dihydroxyPEG or a PEG-acetal). In certain such embodiments, the linear or branched polyalkylene glycol has a molecular weight of from about 1 kDa to about 100 kDa, preferably about 2 kDa to about 60 kDa; about 5 kDa to about 20 kDa; about 10 kDa to about 20 kDa; about 18 kDa to about 60 kDa; and most preferably about 18 kDa to about 22 kDa or about 27 kDa to about 33 kDa, if linear, and a total of about 36 kDa to about 44 kDa, if the polymer has two branches of equal mass.

Bioactive Components

As noted above, the conjugates of the invention comprise one or more PAGs or PAOs, and particularly one or more strands of PEG, covalently attached to one or more bioactive components. Bioactive components to which one or more polymers (or strands thereof) have been covalently attached are referred to herein variously and equivalently as "conjugated bioactive components" or "modified bioactive components." These terms are to be distinguished herein from "unconjugated bioactive components," "initial bioactive components" or "unmodified bioactive components," all of which terms refer to bioactive components that have not had one or more polymers covalently attached thereto. In another aspect, the present invention provides methods and compositions for stabilizing solutions of bioactive components by the admixture of polymers thereto. It is to be understood, however, that an "unconjugated," "unmodified" or "initial" bioactive component may contain other, non-polymer conjugations or modifications when compared to a wild type or native molecule, and would still be considered to be "unconjugated," "unmodified" or "initial" in accordance with the present invention, since the bioactive component would be "unconjugated," "unmodified" or "initial" with respect to the attachment of polymers.

The term "stabilizing" a bioactive component (or "methods of stabilization" or "stabilized bioactive component") indicates that a bioactive component has been stabilized according to the methods of this invention (i.e., a bioactive component to which a polymer has been covalently attached or admixed according to the methods of the invention). Such stabilized bioactive components will exhibit certain altered biochemical and biophysical characteristics when compared to a bioactive component that has not been stabilized (i.e., a bioactive component to which a polymer has not been covalently attached or admixed). Included among such altered biochemical and biophysical parameters, particularly for proteins such as enzymes, may be decreased autolysis and particularly the maintenance of the enzymatic activity of a protein during incubation under certain harsh environmental or experimental conditions. In certain embodiments of the invention, the altered biochemical and biophysical parameters may include, for example, an increased half-life in the circulation in vivo, increased bioavailability, and the like.

Any component (typically a molecule or macromolecular complex) having biological (i.e., physiological, biochemical or pharmaceutical) activity can be suitably used as an initial component in the present invention. Such bioactive components include, but are not limited to, proteins, polypeptides, peptides, therapeutic viruses, organic compounds, and the like. Bioactive components also include fragments, variants and derivatives of such proteins, polypeptides, peptides, therapeutic viruses, organic compounds and the like, particularly such fragments, variants and derivatives having biological (i.e., physiological, biochemical or pharmaceutical) activity.

Suitable organic compounds useful as bioactive components in the present invention include, without limitation, moieties such as taxanes, anthracycline, compounds including daunorubicin, doxorubicin, p-aminoaniline mustard, melphalan, cytosine arabinoside ("Ara-C") and other anti-metabolic compounds, e.g., gemcitabine, etc. Alternatively, the bioactive component can be a cardiovascular agent, antineoplastic, anti-infective, anti-fungal such as nystatin and amphotericin B, anti-anxiety agent, gastrointestinal agent, an agent active in the central nervous system, analgesic, fertility agent, contraceptive agent, anti-inflammatory agent, steroidal agent, anti-uricemic agent, vasodilating agent, vasoconstricting agent, and the like.

Suitable peptides, polypeptides, enzymes and other proteins, glycoproteins and the like that are useful as bioactive components in the present invention include any peptide, polypeptide, enzyme or other protein, etc., having at least one available amino group, thiol group or other group to which polymers can be attached. Such components include materials that have physiological or pharmacological activities, as well as those that are able to catalyze reactions in organic solvents. Peptides, polypeptides and proteins of interest include, but are not limited to, hemoglobin, serum proteins such as blood-clotting factors, e.g., Factors VII, VIII, and IX, immunoglobulins, insulin, cytokines such as interleukins, e.g., IL-1 through IL-18, interferons (e.g., IFN-alpha, IFN-beta, IFN-gamma and consensus IFN), colony stimulating factors including without limitation GM-CSF, G-CSF, macrophage colony stimulating factor, thrombopoietin, megakaryocyte growth and development factor, erythropoietin, platelet derived growth factor, phospholipase-activating protein ("PLAP"), leukemia inhibitory factor ("LIF," also known in the art as "Steel Factor"), neurotrophic factors and stem cell factor and peptide mimetics thereof. Receptor-binding antagonists of bioactive agents are themselves suitable for use as bioactive components of the present invention. Other proteins of general biological or therapeutic interest include insulin, plant proteins such as lectins and ricins, tumor necrosis factors and related proteins, growth factors such as transforming growth factors, e.g., TGF-alpha or TGF-beta, fibroblast growth factors, epidermal growth factors, hepatocyte growth factors, hormones, somatomedins, erythropoietin, pigmentary hormones, hypothalamic releasing factors, antidiuretic hormones, prolactin, chorionic gonadotropin, follicle-stimulating hormone, thyroid-stimulating hormone, prolactin, tissue plasminogen activator, receptor-binding protein antagonists thereof, and the like. Many such proteins exist in both glycosylated and non-glycosylated forms. The non-glycosylated forms may result from their production using recombinant techniques in prokaryotes. Such non-glycosylated products are among the peptides and proteins that are suitable bioactive components of the present invention.

Enzymes of interest include carbohydrate-specific enzymes, proteolytic enzymes, oxidoreductases, transferases, hydrolases, lyases, isomerases and ligases. Without being limited to particular enzymes, examples of enzymes of interest include asparaginase, arginase, arginine deiminase, adenosine deaminase, superoxide dismutase, endotoxinases, catalase, chymotrypsin, lipases, uricases, adenosine diphosphatase, tyrosinases and bilirubin oxidase. Carbohydrate-specific enzymes of interest include glucose oxidases, glucosidases, galactosidases, glucocerebrosidases, glucuronidases and the like.

Also suitable for use as a bioactive component in the conjugates of the present invention is any compound demonstrating bioactivity in vivo. Such compounds include, without limitation, amino acid sequences, nucleic acids (DNA, RNA), peptide nucleic acids ("PNAs"), antibody fragments, single-chain binding proteins (see, e.g., Ladner, R. C., et al., U.S. Pat. No. 4,946,778, the disclosure of which is incorporated herein by reference), binding molecules including soluble receptors, polyclonal antibodies, monoclonal antibodies, catalytic antibodies and the products of fusion of antibodies or fragments thereof.

The proteins or portions thereof can be prepared or isolated by using techniques known to those of ordinary skill in the art such as chemical synthesis, cell, tissue or organ culture, extraction from animal sources, or by recombinant DNA methodologies. Transgenic sources of the amino acid sequences, polypeptides and proteins and the like are also contemplated. Such materials can be obtained from transgenic animals, e.g., mice, rabbits, pigs, goats and cows, wherein the proteins are expressed in milk, blood or tissues, or in the eggs of transgenic birds. Transgenic insects and fungal or baculovirus expression systems are also contemplated as sources. Moreover, mutant versions of proteins are also within the scope of the invention.

Other proteins of interest are allergenic proteins such as ragweed, Antigen E, honeybee venom, mite allergen and the like. The foregoing are illustrative of the proteins that are suitable for the present invention. It is to be understood that other peptides, polypeptides or proteins, or fragments thereof, that are not specifically mentioned herein but that have one or more available amino groups or thiol groups suitable for coupling with one or more polymers according to the invention, are also intended and are within the scope of the present invention.

In a preferred aspect of the invention, the compound that is capable of polymer coupling is a biologically active compound that is suitable for medicinal or diagnostic use in the treatment of animals, e.g., mammals, including humans, for conditions for which such treatment is desired. The foregoing list is meant to be illustrative and not limiting for the compounds that can be modified. Those of ordinary skill will realize that other such compounds can be similarly modified without undue experimentation. It is to be understood that those biologically active materials not specifically mentioned but having one or more available nucleophilic groups such as amino groups or thiols that are accessible for coupling with one or more polymers according to the invention are also intended and are within the scope of the present invention.

It is noted that bioactive components suitable for incorporation into the conjugates of the invention may be substances or compounds that are not active by themselves, while in the conjugate or immediately after hydrolytic release from the conjugate, but that can become active after undergoing a further chemical processing or reaction. For example, an anticancer drug that is delivered to the bloodstream in the form of a conjugate of the present invention may remain inactive until entering a cancer or tumor cell, whereupon it is activated by a chemical process that occurs within the cancer or tumor cell, e.g., by an enzymatic reaction unique to or especially effective in that cell.

Other compounds suitable for use as the bioactive compounds in the conjugates and compositions of the invention include hydroxyl-containing compounds, such as camptothecin and related inhibitors of topoisomerase I. Camptothecin is a water-insoluble cytotoxic alkaloid produced by *Camptotheca accuminata* trees, indigenous to China, and by *Nothapodytes foetida* trees, indigenous to India. Camptothecin and related compounds and analogs are also known to be potential anticancer or antitumor agents and have been shown to exhibit these activities in vitro and in vivo (see, e.g., U.S. Pat. Nos. 4,943,579, 5,004,758 and Re 32,518, the contents of which are incorporated herein by reference). Such compounds and derivatives thereof can be made using known synthetic techniques without undue experimentation. Preferred camptothecin derivatives for use herein include those that include a 20—OH or another hydroxyl group that is capable of reacting directly with activated forms of the polymers such as the monofunctionally activated PEGs of this invention.

Additional hydroxyl-containing moieties suitable for use as bioactive components in the present conjugates include taxanes and paclitaxel derivatives. For purposes of the present invention, the term "taxane" includes all compounds within the taxane family of terpenes. Thus, Taxol (paclitaxel), 3'-substituted t-butoxycarbonyl-amine derivatives (taxoteres) and the like, as well as other analogs that are readily synthesized using standard organic techniques or are available from commercial sources such as Sigma (St. Louis, Mo.), are within the scope of the present invention. These compounds and their derivatives have been found to be effective anticancer agents. Numerous studies indicate that the agents have activity against a variety of malignancies and other cancers.

As the ordinarily skilled artisan will appreciate, any bioactive component known and readily available in the art is suitable for conjugation with monofunctional polymers having reduced antigenicity, substantially reduced antigenicity or undetectable antigenicity, according to the present invention. In accordance with certain aspects of the invention, these initial bioactive components are used to produce conjugates in which one or more PAGs or PAOs are covalently linked to the bioactive molecule. Sites on the initial bioactive component molecules to which polymers may be attached advantageously include lysine residues found on peptide molecules, which residues each have two amino groups. One of these amino groups (the alpha amino group) participates in peptide bond formation (except when the lysine is the amino-terminal residue of the protein), leaving the other amino group (the epsilon amino group) available for polymer coupling. Other sites on protein or peptide molecules to which polymers advantageously may be attached include, among others, the alpha amino group at the amino-terminal residue of the polypeptide; the sulfhydryl groups of cysteine residues on the protein or peptide (Braxton, S. M., U.S. Pat. No. 5,766,897), to which polymers activated with vinyl sulfone, maleimide, iodoacetamide, bromoacetamide or orthopyridyl disulfide, among other thiol-reactive groups that are known in the art, can be coupled; the guanido groups of arginine residues on the protein or peptide (Sano, A., et al., U.S. Pat. No. 5,093, 531), to which polymers activated with phenylglyoxal can be coupled; the alpha carboxyl group of the C-terminal residue, the beta carboxyl groups of aspartate residues on the protein or peptide and the gamma carboxyl groups of the glutamate residues on the protein or peptide (Sakane, T., et al. (1997) *Pharm Res* 14:1085-1091), to which amino or hydrazide derivatives of the polymer can be coupled. Of course, other suitable sites on the protein or peptide molecule to which one or more polyalkylene oxides may be attached advantageously will be readily apparent to one of ordinary skill in the art, particularly upon consideration of the primary and tertiary structures of the peptide and the disclosures herein.

Before coupling a polymer to a target bioactive component (e.g., a protein), it can be advantageous to purify the component to remove contaminants; otherwise, the analysis of the extent of modification of the intact component can be complicated by the formation of polymer conjugates of the fragments of the component and other contaminants. Purification of the bioactive component may be advantageous regardless of whether the protein to be conjugated has been obtained from natural sources or produced by recombinant methods, since contaminants in the preparations can be expected from either source. Purification of a given bioactive component can be accomplished by any art-known method that will be familiar to the ordinarily skilled artisan, including but not limited to electrophoresis, dialysis, salt extraction (such as ammonium sulfate precipitation), chromatography (such as affinity chromatography, ion-exchange chromatography, size-exclusion chromatography, high performance liquid chromatography ("HPLC"), fast protein liquid chromatography ("FPLC") and the like) or a combination thereof. It is to be understood, however, that purification of a given bioactive component is not essential for preparation of the polymer-bioactive component conjugates of the present invention, since bioactive components (especially proteins) in crude preparations can also be advantageously conjugated with polymers according to the methods of the present invention.

Coupling of Polymers to Bioactive Components

The PAGs employed in the practice of the present invention, which, as indicated above, are preferably activated by reaction with a coupling group, can be attached to any of several groups that may be present on the bioactive component molecule, e.g., carboxyl groups or amino groups that are not involved in peptide bonds, thiol groups and phenolic hydroxyl groups. For certain peptides or proteins, it is preferred that the activated PAGs be coupled to the N-terminal alpha amino group and/or to the amino groups of lysine residues and/or to the sulfhydryl groups of cysteine residues.

The crude or purified bioactive component (e.g., protein) can be incubated with activated polymer in a buffer having a pH in the range of about 11 or the highest pH at which any inactivation of the protein caused by alkalinity can be reversed, down to about pH 5 or the lowest pH at which any inactivation of the protein caused by acidity can be reversed (see Arakawa, T., et al. (1990) *Biopolymers* 29:1065-1068). As is known in the art, and as one of ordinary skill will readily recognize, the use of a low pH for polymer coupling to proteins can be desirable for certain proteins or linkage chemistries. However, the use of a higher pH can be advantageous for certain other proteins and certain coupling chemistries, depending on the effects of pH on the solubility and stability of the protein and on the rate of inactivation of the activated polymer (whether spontaneous or catalyzed by the protein itself) relative to the rate of attachment of the polymer to the target protein according to methods that are known in the art.

The reaction between the PAG and the bioactive component is normally carried out in solution, preferably an aqueous buffer solution providing a pH in the range of from about 5 to about 11. Particularly preferred for coupling a PAG to a proteinaceous bioactive component (e.g., a polypeptide, peptide, protein, or fragments thereof) are pH values of from about 7 to about 9, most preferably from about 7 to about 8. In other embodiments, pH values of about 4.5 to about 6.5 are preferred. Examples of buffer solutions that will provide pH values in these ranges at 25° C. include, but are not limited to:

50 mL of 0.1 molar potassium dihydrogen phosphate+5.6 to 46.1 mL 0.1 molar NaOH, diluted to 100 mL 50 mL of 0.025 molar borate+2.0 to 20.5 mL 0.1 molar HCl, diluted to 100 mL 50 mL of 0.025 molar borate+0.9 to 18.3 mL 0.1 molar NaOH, diluted to 100 mL 50 mL of 0.05 molar sodium bicarbonate+5.0 to 10.7 mL 0.1 molar NaOH, diluted to 100 mL 50 mL of 0.05 molar acetic acid+5.0 to 30 mL 0.1 molar NaOH, diluted to 100 mL 50 mL of 0.05 molar Tris HCl+10 to 50 mL 0.1 molar Tris base, diluted to 100 mL The precise adjustment of the quantity of acid or base to be used to provide a particular desired pH will be readily determinable by those skilled in the art.

If, in a given instance, the use of a biological buffer should be required, one of the following may be employed:

Hydroxyethylpiperizine-ethane sulfonic acid ("HEPES")
3-(N-Morpholino)propane sulfonic acid ("MOPS")
3-(N-Morpholino)-2-hydroxypropane sulfonic acid ("MOPSO")
Piperazine-N,N'-bis(2-hydroxypropane sulfonic acid) ("POPSO")

The reaction between the PAG and the bioactive component will normally be performed under conditions that will not give rise to inactivation or denaturation, e.g., at temperatures at which the bioactive component retains substantial bioactivity and subject to no more agitation than necessary to assure adequate mixing of the reactants. The reaction between the PAG and bioactive proteins will preferably be conducted at a temperature in the range of from about 4° C. to about 40° C. More preferably, the reaction will be conducted at between about 4° C. and 8° C. or at room temperature, i.e. from about 20° C. to about 25° C. The reactions between the PAG and non-protein bioactive agents, e.g., peptides and bioactive organic chemicals, may be carried out at higher or lower temperatures that are compatible with the stability of the particular bioactive organic chemical that is being coupled to the PAG.

It will be readily understood by those skilled in the art that the amount of PAG employed relative to the amount of bioactive component will be dependent upon the desired extent of polymer coupling to the bioactive component. For example, when it is desired to react a PAG with a particular fraction of the solvent-accessible lysine residues (in cases where the bioactive component is a polypeptide), a molar concentration of PAG at least equal to that of the lysines to be coupled will be required. Clearly, if fewer than all of the solvent-accessible reaction sites on the bioactive component molecule are to be derivatized, correspondingly less PAG will be required. In general, however, where molar excesses of PAGs are used, the present inventors have determined that molar excesses on the order of 2 to 10 can be preferred.

The time required for the reaction will depend upon a number of factors, such as reaction temperature, the concentrations of reactants, and the extent of derivatization desired. The course of the reaction can be monitored by conventional means, such as the periodic analysis of samples by sizeexclusion chromatography or gel electrophoresis. The reaction can be terminated conveniently when desired by the addition of a low molecular weight compound having a reactive group, e.g., glycine, to scavenge excess amine-reactive PAG or by chromatographic fractionation. At room temperature, reaction time of about 15 minutes to about 24 hours will typically be required to react the PAG with the binding groups of most bioactive components (e.g., the lysine groups of polypeptide chains). Longer reaction times may be required at lower temperatures. The skilled practitioner will understand that the time for conjugation, as well as the amount and type of PAG, must not be such as to inactivate the bioactive component being employed, i.e., must not result in substantial loss of the biological activity of the bioactive component. By "not resulting in substantial loss of biological activity of the bioactive component" it is meant that the PAG-conjugated bioactive component demonstrates at least about 10%, preferably at least about 20%, 35%, 50%, 75%, 90%, 92%, 94%, 95%, 96%, 97%, 98%, 99% or more of the level of bioactivity (e.g., enzymatic activity; receptor binding ability; anti-neoplastic activity; etc.) that is demonstrated in vitro or in vivo by the same bioactive component that has not been conjugated with a PAG.

Purification of the polymer-coupled bioactive component can be effected by means commonly employed by those skilled in the art, such as, for example, size-exclusion chromatography, ion-exchange chromatography, ultrafiltration, dialysis, and the like. Solutions of the reaction product can, if desired, be concentrated with a rotary evaporator and the product can be obtained in the dry state by lyophilization.

Depending upon the particular bioactive component used and the extent to which it is reacted with the PAG, the resulting adduct is expected to be useful diagnostically or therapeutically, exhibiting, as compared to the unreacted bioactive component, decreased antigenicity and immunogenicity, increased circulating life, and increased stability, while maintaining a useful level of biological activity.

The bioactive component can be reacted with the monofunctionally activated branched poly(ethylene glycol) polymers discussed above (particularly one or more monofunctionally activated, branched dihydroxyPEGs, e.g., dihydroxyPEG-lysine) in an aqueous reaction medium that can be buffered, depending on the pH requirements of the nucleophile and the activated polymer. The optimal pH for the reaction is generally between about 6.5 and about 8.5 and preferably about 7.4 for maintaining the solubility and stability of most polypeptides. The optimal pH for coupling an activated PAG, e.g., NPC-PEG, to a mammalian uricase is approximately pH 10, while the optimal pH for selectively coupling certain activated PAGs to the N-terminal alpha amino group of a protein or peptide is in the range of about 4 to about 7. The optimal reaction conditions necessary to maintain the stability of the bioactive component, the reaction efficiency, etc., are within the level of ordinary skill in the art. The preferred temperature range is between about 4° C. and about 40° C. The reaction temperature must not exceed the temperature at which the nucleophile may denature or decompose. It is preferred that the nucleophile be reacted with an excess of the activated branched polymer. Following the reaction, the conjugate is recovered and purified, for example, by diafiltration, column chromatography, combinations thereof, or the like.

The use of molecular modeling can facilitate a strategy for the optimization of polymer coupling to a protein. For example, X-ray crystallographic data can be used to generate computerized images of the solvent-accessible surfaces of proteins (Sayle, R. A., et al. (1995) *Trends Biochem Sci* 20:374-376). Structural analyses that are based on nuclear magnetic resonance measurements can also be useful in this regard. The fraction of the accessible sites on the surface with which a particular activated polymer can react, and the distribution of polymer strands among the various sites, can be modulated by selecting the appropriate activating group, the molar ratio of the polymer to the protein and the appropriate conditions of the coupling reaction (e.g., pH, temperature, concentrations of reactants, duration of incubation). In certain circumstances, it can be advantageous to attach the polymer to residues that are sufficiently far from the active site of an enzyme to minimize any adverse effects on bioactivity. For example, the surface of Proteinase K contains many potential sites for the attachment of polymers that are activated with various chemistries. However, the previous discovery by some of the present inventors that the most solvent-accessible lysine residues of Proteinase K are located exclusively in a region of the enzyme that is relatively far from the catalytic site makes the use of amine-reactive polymers especially desirable for this particular enzyme (see commonly owned, copending U.S. patent application Ser. No. 10/183,607, filed Jun. 28, 2002, which is incorporated herein by reference in its entirety).

In certain embodiments (e.g., in the case of enzymes in which the catalytic domain contains amino groups (such as those described above) with which the activated polymer can react), it may be desirable to shield the active site from contact with the activated polymer. In such cases, the enzyme can be bound tightly, but reversibly, to a substrate analog or competitive inhibitor that is sufficiently large to sterically hinder the access of the activated polymer to reactive residues within or near the active site (see, e.g., Nahri, L. O., et al. (1991) *J Protein Chem* 10:385-389). Alternatively, such analogs or inhibitors can be bound to a solid matrix to which the protein can be subsequently adsorbed. While bound to the resultant "affinity matrix," the protein can be reacted with the activated polymer. This strategy can minimize the coupling of the reactive polymer to sites where such coupling might inhibit catalysis. The selectively modified protein can be released from the affinity matrix subsequently, by methods that are known to those skilled in the art (see Wilchek, M., et al. (1984) *Methods Enzymol* 104:3-55). The resultant conjugates can include protein molecules to which the polymer is preferentially attached at sites where it does not interfere with the bioactivity of the protein.

Following the coupling reaction, conjugates that are derivatized to various extents can be separated from each other using size-exclusion and/or ion-exchange chromatography, as described by Sherman, M. R., et al. (1997) supra. For example, chromatography on a Superdex® 75 brand HR 10/30 column or a Superdex® 200 brand HR 10/30 column (Amersham Pharmacia Biotech, Piscataway, N.J.) permits the separation of protein molecules that are PEGylated to different extents, as well as their separation from residual free PEG and from most byproducts of the coupling reaction (see commonly owned, co-pending U.S. patent application Ser. No. 10/183,607, supra).

Compositions

The invention provides stabilized conjugates of PEGylated bioactive components of decreased antigenicity produced by the methods of this invention. In related aspects, the invention also provides compositions comprising one or more such conjugates. Compositions according to this aspect of the invention will comprise one or more (e.g., one, two, three, four, five, ten, etc.) of the above-described conjugates of the invention. In certain such aspects, the compositions may comprise one or more additional components, such as one or more buffer salts, one or more chaotropic agents, one or more detergents, one or more proteins (e.g., one or more enzymes), one or more polymers and the like. The compositions of this aspect of the invention may be in any form, including solid (e.g., dry powder) or solution (particularly in the form of a physiologically compatible buffered salt solution comprising one or more of the conjugates of the invention).

Pharmaceutical Compositions

Certain compositions of the invention are particularly formulated for use as pharmaceutical compositions for use in prophylactic, diagnostic or therapeutic applications. Such compositions will typically comprise one or more of the conjugates of the invention and one or more pharmaceutically acceptable carriers or excipients. The term "pharmaceutically acceptable carrier or excipient," as used herein, refers to a non-toxic solid, semisolid or liquid filler, diluent, encapsulating material or formulation auxiliary of any type that is capable of being tolerated by a recipient animal, including a human or other mammal, into which the pharmaceutical composition is introduced, without adverse effects resulting from its addition.

The pharmaceutical compositions of the invention may be administered to a recipient via any suitable mode of administration, such as orally, rectally, parenterally, intrasystemically, vaginally, intraperitoneally, topically (as by powders, ointments, drops or transdermal patch), buccally, as an oral or nasal spray or by inhalation. The term "parenteral" as used herein refers to modes of administration that include intravenous, intramuscular, intraperitoneal, intracisternal, subcutaneous and intra-articular injection and infusion.

Pharmaceutical compositions provided by the present invention for parenteral injection can comprise pharmaceutically acceptable sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, poly(ethylene glycol), and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

Such pharmaceutical compositions of the present invention may also contain adjuvants such as preservatives, wetting agents, emulsifying agents and dispersing agents. Prevention of the action of microorganisms may be ensured by the inclusion of various antibacterial and antifungal agents, for example, paraben, benzyl alcohol, chlorobutanol, phenol, sorbic acid, and the like. It may also be desirable to include osmotic agents such as sugars, sodium chloride and the like. Prolonged absorption of the injectable pharmaceutical form may be brought about by the inclusion of agents that delay absorption, such as aluminum monostearate, hydrogels and gelatin.

In some cases, in order to prolong the effect of the drugs, it is desirable to slow the absorption from subcutaneous or intramuscular injection. This may be accomplished by the use of a liquid suspension of crystalline or amorphous material with poor solubility in aqueous body fluids. The rate of absorption of the drug then depends upon its rate of dissolution, which, in turn, may depend upon its physical form. Alternatively, delayed absorption of a parenterally administered drug form is accomplished by dissolving or suspending the drug in an oil vehicle.

Injectable depot forms are made by forming microencapsulated matrices of the drug in biodegradable polymers such as polylactide-polyglycolide. Depending upon the ratio of drug to carrier polymer and the nature of the particular carrier polymer employed, the rate of drug release can be controlled. Examples of other biodegradable polymers include biocompatible poly(orthoesters) and poly(anhydrides). Depot injectable formulations are also prepared by entrapping the drug in liposomes or microemulsions that are compatible with body tissues.

The injectable formulations can be sterilized, for example, by filtration through a bacteria-retaining filter, or by incorporating sterilizing agents in the form of sterile solid compositions that can be dissolved or dispersed in sterile water or other sterile injectable medium prior to use.

Solid dosage forms for oral administration include capsules, tablets, pills, powders and granules. In such solid dosage forms, the active compounds are mixed with at least one pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and gum acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) accelerators of absorption, such as quaternary ammonium compounds, g) wetting agents such as, for example, cetyl alcohol and glycerol monostearate, h) adsorbents such as kaolin and bentonite clay, and i) lubricants such as talc, calcium stearate, magnesium stearate, solid poly(ethylene glycols), sodium lauryl sulfate, and mixtures thereof. In the case of capsules, tablets and pills, the dosage form may also comprise buffering agents.

Solid compositions of a similar type may also be employed as fillers in soft- and hard-filled gelatin capsules using such excipients as lactose (milk sugar) as well as high molecular weight PEGs and the like.

The solid dosage forms of tablets, dragees, capsules, pills and granules can be prepared with coatings and shells such as enteric or chronomodulating coatings and other coatings well known in the pharmaceutical formulating art. They may optionally contain opacifying agents and can also be of such a composition that they release the active ingredient(s) only, or preferentially, in a certain part of the gastrointestinal tract, optionally, in a delayed manner. Examples of embedding compositions that can be used include polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, PEGs and fatty acid esters of sorbitan, and mixtures thereof.

In addition to inert diluents, the oral compositions can also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredients in finely divided form may be used in admixture with a larger-sized pharmaceutically acceptable inert carrier comprising particles having a size, for example, of up to 100 micrometers in diameter. Suitable inert carriers include sugars such as lactose and sucrose. Desirably, at least 95% by weight of the particles of the active ingredient have an effective particle size in the range of 0.01 to 10 micrometers.

Alternatively, the pharmaceutical composition may be pressurized and contain a compressed gas, such as nitrogen or a liquefied gas propellant. The liquefied propellant medium and indeed the total composition may be preferably such that the active ingredients do not dissolve therein to any substantial extent. The pressurized composition may also contain a surface-active agent. The surface-active agent may be a liquid or solid non-ionic surface-active agent or may be a solid anionic surface-active agent. It is preferable to use the solid anionic surface-active agent in the form of a sodium salt.

A further form of topical administration is to the eye. In this mode of administration, the conjugates or compositions of the invention are delivered in a pharmaceutically acceptable ophthalmic vehicle, such that the active compounds are maintained in contact with the ocular surface for a sufficient time period to allow the compounds to penetrate the conjunctiva or the corneal and internal regions of the eye, as for example the anterior chamber, posterior chamber, vitreous body, aqueous humor, vitreous humor, cornea, iris/ciliary, lens, choroid/retina and sclera. The pharmaceutically acceptable ophthalmic vehicle may, for example, be an ointment, vegetable oil or an encapsulating material.

Compositions for rectal or vaginal administration are preferably suppositories that can be prepared by mixing the conjugates or compositions of the invention with suitable non-irritating excipients or carriers such as cocoa butter, PEG or a suppository wax, which are solid at room temperature but liquid at body temperature and therefore melt in the rectum or vaginal cavity and release the drugs.

The pharmaceutical compositions used in the present therapeutic methods may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. In addition to one or more of the conjugates or compositions of the invention, the present pharmaceutical compositions in liposomal form can also contain one or more stabilizers, preservatives, excipients, and the like. The preferred lipids are the phospholipids and the phosphatidyl cholines (lecithins), both natural and synthetic. Methods to form liposomes are known in the art (see, e.g., Zalipsky, S., et al., U.S. Pat. No. 5,395,619). Liposomes that comprise phospholipids that are conjugated to PEG, most commonly phosphatidyl ethanolamine coupled to mPEG, have advantageous properties, including prolonged lifetimes in the blood circulation of mammals (Fisher, D., U.S. Pat. No. 6,132,763). More advantageously, the hydroxyPEGs of the present invention may be substituted for MPEG in forming such PEG-liposomes. Most advantageously, the monofunctionally activated hydroxyPEGs of the present invention may be substituted for activated mPEGs in the synthesis of PEG-diacylglycerol that is to be incorporated into PEG-liposomes.

Dose Regimens

The conjugates or compositions of the invention can be administered in vitro, ex vivo or in vivo to cells to enhance the cellular response to the active compound(s). One of ordinary skill will appreciate that effective amounts of a given active compound, conjugate or composition can be determined empirically and may be employed in pure form or, where such forms exist, in pharmaceutically acceptable formulation or prodrug form. The compounds, conjugates or compositions of the invention may be administered to an animal or human patient in need thereof as veterinary or pharmaceutical compositions in combination with one or more pharmaceutically acceptable excipients. It will be understood that, when administered to a human patient, the total daily, weekly or monthly usage of the compounds and compositions of the present invention will be decided by the attending physician within the scope of sound medical judgment. The therapeutically effective dose level for any particular patient will depend upon a variety of factors including the type and degree of the cellular response to be achieved; the identity and/or activity of the specific compound(s), conjugate(s) or composition(s) employed; the age, body weight or surface area, general health, gender, diet and activity level of the patient; the time of administration, route of administration, and rate of excretion of the active compound(s); the duration of the treatment; other drugs used in combination or coincidental with the specific compound(s), conjugate(s) or composition(s); and like factors that are well known to those of ordinary skill in the pharmaceutical and medical arts. For example, it is well within the skill of the art to start doses of a given compound, conjugate or composition of the invention at levels lower than those required to achieve the desired therapeutic effect and to gradually increase the dosages until the desired effect is achieved.

Dose regimens may also be arranged in a patient-specific manner to provide a predetermined concentration of a given active compound in the blood, as determined by techniques accepted and routine in the art, e.g., size-exclusion, ion-exchange or reversed-phase HPLC. Thus, patient dose regimens may be adjusted to achieve relatively constant blood levels, as measured by HPLC, according to methods that are routine and familiar to those of ordinary skill in the medical, pharmaceutical and/or pharmacological arts.

Diagnostic and Therapeutic Uses

A diagnostic use of a conjugate of the invention might be for locating an antigenic moiety, e.g., a cancer, within the body of an animal, especially a human, by administration of a polymer-conjugated antibody of the invention, in which the conjugate is labeled on either the protein or polymer component to enable detection, e.g., by optical, radiometric, fluorescent or resonant detection as discussed below.

The PAG-bioactive compound conjugates (preferably administered as compositions comprising such conjugates) of the present invention are expected to have much longer circulating half lives and reduced antigenicity and immunogenicity in vivo. These properties alleviate or ameliorate the rapid clearance from the circulation that is observed when many therapeutic compounds (particularly bioactive compounds such as those that are used as components in the conjugates of the present invention) are introduced into an animal, especially a human or other mammal, for therapeutic purposes. Use of the conjugates and compositions of the invention also reduces or eliminates concerns about repeated administration of a particular bioactive compound or component, which may otherwise provoke an immune response in the patient. Immune responses of concern include those that neutralize the bioactivity and/or increase the rate of clearance of the bioactive compound from the circulation (thereby decreasing the effectiveness of the diagnostic or therapeutic procedure) and those that cause adverse effects on the patient.

Hence, in another aspect of the invention, the conjugates and compositions of the invention may be used in diagnostic or therapeutic methods, for example in diagnosing, treating or preventing a variety of physical disorders in an animal, particularly a mammal such as a human, predisposed to or suffering from such a disorder. In such approaches, the goal of the therapy is to delay or prevent the development of the disorder, and/or to cure or induce a remission of the disorder, and/or to decrease or minimize the side effects of other therapeutic regimens. Hence, the PAG-bioactive component conjugates and compositions of the present invention may be used for protection, suppression or treatment of physical disorders, such as infections or diseases. The term "protection" from a physical disorder, as used herein, encompasses "prevention," "suppression" and "treatment." "Prevention" involves the administration of a conjugate or composition of the invention prior to the induction of the disease or physical disorder, while "suppression" involves the administration of the conjugate or composition prior to the clinical appearance of the disease; hence, "prevention" and "suppression" of a physical disorder typically are undertaken in an animal that is predisposed to or susceptible to the disorder, but that is not yet suffering therefrom. "Treatment" of a physical disorder, however, involves administration of the therapeutic conjugate or composition after the appearance of the disease. It will be understood that in human and veterinary medicine, it is not always possible to distinguish between "preventing" and "suppressing" a physical disorder. In many cases, the ultimate inductive event or events may be unknown or latent, and neither the patient nor the physician may be aware of the inductive event until well after its occurrence. Therefore, it is common to use the term "prophylaxis," as distinct from "treatment," to encompass both "preventing" and "suppressing" as defined herein. The term "protection," used in accordance with the methods of the present invention, therefore is meant to include "prophylaxis."

Methods according to this aspect of the invention may comprise one or more steps that allow the clinician to achieve the above-described therapeutic goals. One such method of the invention may comprise, for example:
(a) identifying an animal (preferably a mammal, such as a human) suffering from or predisposed to a physical disorder; and
(b) administering to the animal an effective amount of one or more of the compounds or compositions of the invention as described herein, particularly one or more PAG conjugates of a bioactive component (or one or more pharmaceutical compositions comprising such conjugates), such that the administration of the compounds or compositions prevents, delays or diagnoses the development of, or cures or induces remission of, the physical disorder in the animal.

As used herein, an animal that is "predisposed to" a physical disorder is defined as an animal that does not exhibit a plurality of overt physical symptoms of the disorder but that is genetically, physiologically or otherwise at risk for developing the disorder. In the present methods, the identification of an animal (such as a mammal, including a human) that is predisposed to, at risk for, or suffering from a given physical disorder may be accomplished according to standard art-known methods that will be familiar to the ordinarily skilled clinician, including, for example, radiological assays, biochemical assays (e.g., assays of the relative levels of particular peptides, proteins, electrolytes, etc., in a sample obtained from an animal), surgical methods, genetic screening, family history, physical palpation, pathological or histological tests (e.g., microscopic evaluation of tissue or bodily fluid samples or smears, immunological assays, etc.), testing of bodily fluids (e.g., blood, serum, plasma, cerebrospinal fluid, urine, saliva, semen and the like), imaging, (e.g., radiologic, fluorescent, optical, resonant (e.g., using nuclear magnetic resonance (NMR) or electron spin resonance (ESR)), etc. Once an animal has been identified by one or more such methods, the animal may be aggressively and/or proactively treated to prevent, suppress, delay or cure the physical disorder.

Physical disorders that can be prevented, diagnosed or treated with the conjugates, compositions and methods of the present invention include any physical disorders for which the bioactive component of the conjugate may be used in the prevention, diagnosis or treatment. Such disorders include, but are not limited to, a variety of cancers (e.g., breast cancers, uterine cancers, ovarian cancers, prostate cancers, testicular cancers, leukemias, lymphomas, lung cancers, neurological cancers, skin cancers, head and neck cancers, bone cancers, colon and other gastrointestinal cancers, pancreatic cancers, bladder cancers, kidney cancers and other carcinomas, sarcomas, adenomas and myelomas); infectious diseases (e.g., bacterial diseases, fungal diseases, viral diseases (including hepatitis and HIV/AIDS), parasitic diseases, and the like); genetic disorders (e.g., cystic fibrosis, amyotrophic lateral sclerosis, muscular dystrophy, Gaucher's disease, Pompe's disease, severe combined immunodeficiency disorder and the like), anemia, neutropenia, hemophilia and other blood disorders; neurological disorders (e.g., multiple sclerosis and Alzheimer's disease); enzymatic disorders (e.g., gout, uremia, hypercholesterolemia, and the like); disorders of uncertain etiology (e.g., cardiovascular disease, hypertension, and the like); and other disorders of medical importance that will be readily familiar to the ordinarily skilled artisan. The compositions and methods of the present invention may also be used in the prevention of disease progression, such as in chemoprevention of the progression of a premalignant lesion to a malignant lesion.

The therapeutic methods of the invention thus use one or more conjugates of the invention, or one or more of the pharmaceutical compositions of the invention that may be administered to an animal in need thereof by a variety of routes of administration, including orally, rectally, parenterally (including intravenously, intramuscularly, intraperitoneally, intracisternally, subcutaneously and intra-articular injection and by infusion), intrasystemically, vaginally, intraperitoneally, topically (as by powders, ointments, drops or transdermal patch), buccally, as an oral or nasal spray or by inhalation. By the invention, an effective amount of the conjugates or compositions can be administered in vitro, ex vivo or in vivo to cells or to animals suffering from or predisposed to a particular disorder, thereby preventing, delaying, diagnosing or treating the disorder in the animal. As used herein, "an effective amount of a conjugate (or composition)" refers to an amount such that the conjugate carries out the biological activity of the bioactive component of the conjugate, thereby preventing, delaying, diagnosing, treating or curing the physical disorder in the animal to which the conjugate of the invention has been administered. One of ordinary skill will appreciate that effective amounts of the conjugates or compositions of the invention can be determined empirically, according to standard methods well-known to those of ordinary skill in the pharmaceutical and medical arts; see, e.g., Beers, M. H., et al., eds. (1999) *Merck Manual of Diagnosis & Therapy,* 17th edition, Merck and Co., Rahway, N.J.; Hardman, J. G., et al., eds. (2001) *Goodman and Gilman's The Pharmacological Basis of Therapeutics,* 10th edition, McGraw-Hill Professional Publishing, Elmsford, N.Y.; Speight, T. M., et al., eds. (1997) *Avery's Drug Treatment: Principles and Practice of Clinical Pharmacology and Therapeutics,* 4th edition, Blackwell Science, Inc., Boston; Katzung, B. G. (2000) *Basic and Clinical Pharmacology,* 8th edition, Appleton and Lange, Norwalk, Conn.; which references and references cited therein are incorporated entirely herein by reference.

It will be understood that, when administered to a human patient, the total daily, weekly or monthly dosage of the conjugates and compositions of the present invention will be decided by the attending physician within the scope of sound medical judgment. For example, satisfactory results are obtained by administration of certain of the conjugates or compositions of the invention at appropriate dosages depending on the specific bioactive compound used, which dosages will be readily familiar to the ordinarily skilled artisan or which may be readily determined empirically using only routine experimentation. According to this aspect of the invention, the conjugates or compositions can be administered once or, in divided doses, e.g., twice per day or per week or per month. Appropriate dose regimens for various modes of administration (e.g., parenteral, subcutaneous, intramuscular, intra-ocular, intranasal, etc.) can also be readily determined empirically, using only routine experimentation, or will be readily apparent to the ordinarily skilled artisan, depending on the identity of the bioactive component.

In additional applications, the conjugates and compositions of the invention may be used to specifically target a diagnostic or therapeutic agent to a cell, tissue, organ or organism that expresses a receptor for, binds, incorporates or otherwise can take up, the bioactive component of the conjugate. Methods according to this aspect of the invention may comprise, for example, contacting the cell, tissue, organ or organism with one or more conjugates of the invention, which conjugates additionally comprise one or more diagnostic or therapeutic agents (preferably covalently linked to the PAO or PEG component of the conjugate), such that the conjugate is taken up by the cell, tissue, organ or organism by any mechanism (e.g., by receptor-mediated endocytosis, pinocytosis, phagocytosis, diffusion, etc.), thereby delivering the diagnostic or therapeutic agent to the cell, tissue, organ or organism. The diagnostic or therapeutic agent used in accordance with this aspect of the invention may be, but is not limited to, at least one agent selected from a nucleic acid, an organic compound, a protein, an antibody, an enzyme, a glycoprotein, a lipoprotein, an element, a lipid, a saccharide, an isotope, a carbohydrate, an imaging agent, a detectable probe, or any combination thereof, which also may be detectably labeled as described herein. A therapeutic agent used in this aspect of the present invention may have a therapeutic effect on the target cell (or tissue, organ or organism), the effect being selected from, but not limited to, correcting a defective gene or protein, a drug action, a toxic effect, a growth-stimulating effect, a growth-inhibiting effect, a metabolic effect, a catabolic affect, an anabolic effect, an antiviral effect, an antifungal effect, an antibacterial effect, a hormonal effect, a neurohumoral effect, a cell differentiation stimulatory effect, a cell differentiation inhibitory effect, a neuromodulatory effect, an anti-neoplastic effect, an anti-tumor effect, an insulin stimulating or inhibiting effect, a bone marrow stimulating effect, a pluripotent stem cell stimulating effect, an immune system stimulating effect, and any other known therapeutic effect that may be provided by a therapeutic agent delivered to a cell (or tissue, organ or organism) via a delivery system according to this aspect of the present invention.

Such additional therapeutic agents, which can further comprise a bioactive conjugate or composition of the present invention, may be selected from, but are not limited to, known and new compounds and compositions including antibiotics, steroids, cytotoxic agents, vasoactive drugs, antibodies and other therapeutic agents. Non-limiting examples of such agents include antibiotics and other drugs used in the treatment of bacterial shock, such as gentamycin, tobramycin, nafcillin, parenteral cephalosporins, etc.; adrenal corticosteroids and analogs thereof, such as dexamethasone, which mitigate the cellular injury caused by endotoxins; vasoactive drugs, such as an alpha adrenergic receptor blocking agent (e.g., phenoxybenzamine), a beta adrenergic receptor agonist (e.g., isoproterenol), and dopamine.

The conjugates and compositions of the invention may also be used for the diagnosis of disease and to monitor therapeutic response. In certain such methods, the conjugates of the invention may comprise one or more detectable labels (such as those described elsewhere herein). In specific such methods, these detectably labeled conjugates of the invention may be used to detect cells, tissues, organs or organisms expressing receptors for, or otherwise taking up, the bioactive component of the conjugates. In one example of such a method, the cell, tissue, organ or organism is contacted with one or more of the detectably labeled conjugates of the invention under conditions that favor the uptake of the conjugate by the cell, tissue or organism (e.g., by binding of the conjugate to a cell-surface receptor or by pinocytosis or diffusion of the conjugate into the cell), and then detecting the conjugate bound to or incorporated into the cell using detection means specific to the label used (e.g., fluorescence detection for fluorescently labeled conjugates; magnetic resonance imaging for magnetically labeled conjugates; radioimaging for radiolabeled conjugates; etc.). Other uses of such detectably labeled conjugates may include, for example, imaging a cell, tissue, organ or organism, or the internal structure of an animal (including a human), by administering an effective amount of a labeled form of one or more of the conjugates of the invention and measuring detectable radiation associated with the cell, tissue, organ or organism (or animal). Methods of detecting various types of labels and their uses in diagnostic and therapeutic imaging are well known to the ordinarily skilled artisan, and are described elsewhere herein.

In another aspect, the conjugates and compositions of the invention may be used in methods to modulate the concentration or activity of a specific receptor for the bioactive component of the conjugate on the surface of a cell that expresses such a receptor. By "modulating" the activity of a given receptor it is meant that the conjugate, upon binding to the receptor, either activates or inhibits the physiological activity (e.g., the intracellular signaling cascade) mediated through that receptor. While not intending to be bound by any particular mechanistic explanation for the regulatory activity of the conjugates of the present invention, such conjugates can antagonize the physiological activity of a cellular receptor by binding to the receptor via the bioactive component of the conjugate, thereby blocking the binding of the natural agonist (e.g., the unconjugated bioactive component) and preventing activation of the receptor by the natural agonist, while not inducing a substantial activation of the physiological activity of the receptor itself. Methods according to this aspect of the invention may comprise one or more steps, for example contacting the cell (which may be done in vitro or in vivo) with one or more of the conjugates of the invention, under conditions such that the conjugate (i.e., the bioactive component portion of the conjugate) binds to a receptor for the bioactive component on the cell surface but does not substantially activate the receptor. Such methods will be useful in a variety of diagnostic, and therapeutic applications, as the ordinarily skilled artisan will readily appreciate.

Kits

The invention also provides kits comprising the conjugates and/or compositions of the invention. Such kits typically comprise a carrier, such as a box, carton, tube or the like, having in close confinement therein one or more containers, such as vials, tubes, ampuls, bottles and the like, wherein a first container contains one or more of the conjugates and/or compositions of the present invention. The kits encompassed by this aspect of the present invention may further comprise one or more additional components (e.g., reagents and compounds) necessary for carrying out one or more particular applications of the conjugates and compositions of the present invention, such as one or more components useful for the diagnosis, treatment or prevention of a particular disease or physical disorder (e.g., one or more additional therapeutic compounds or compositions, one or more diagnostic reagents, one or more carriers or excipients, and the like), one or more additional conjugates or compositions of the invention, and the like.

It will be readily apparent to one of ordinary skill in the relevant arts that other suitable modifications and adaptations to the methods and applications described herein may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

Preparation and Testing of Antibodies to MonomethoxyPEG

It has been reported previously that rabbits can be immunized to various PEGs by immunizing the animals with conjugates in which PEG was coupled to an immunogenic carrier protein (Richter, A. W., et al. (1983) Int Arch Allergy Appl Immunol 70:124-131). A monoclonal antibody that reacts with the polyether backbone of PEG has been developed by injecting mice with an mPEG conjugate of β-glucuronidase and selecting hybridoma clones that produce antibodies to PEG (Cheng, T-L., et al. (1999), supra; Cheng, T L., et al. (2000), supra; Tsai, N.-M., et al. (2001), supra.; Roffler, S., et al., published U.S. Patent Application No. 2001/0028881 A1 and U.S. Pat. Nos. 6,596,849 and 6,617,118; the disclosures of all of which are incorporated herein by reference in their entireties). Another monoclonal antibody that reacts with the polyether backbone of PEG has been disclosed recently by Roberts, M. J., et al., in U.S. Patent Application No. 2003/001704 A1.

In order to develop sensitive methods for the detection of PEG in PEG-protein conjugates, polyclonal antibodies against PEG were prepared as described below. Since nearly all PEG conjugates of therapeutic proteins described in the art have been synthesized with mPEG, the present inventors investigated the role of the methoxyl group in the immunoreactivity of conjugates containing MPEG. The p-nitrophenyl carbonate derivative of 10-kDa mPEG was custom synthesized by Shearwater Corporation (Huntsville, Ala.), a subsidiary of Nektar Therapeutics (San Carlos, Calif.). A urethane-linked MPEG conjugate of a recombinant mammalian uricase was prepared that contained the minimum number of strands of this 10-kDa MPEG needed to solubilize the protein at physiological pH (approximately two strands of PEG or mPEG per 35-kDa uricase subunit). This amount of PEG was not sufficient to suppress the unusually high immunogenicity of uricase (see Sherman, M. R., et al., PCT publication WO 01/59078 A2, and Kelly, S. J., et al. (2001) supra, the disclosures of which are incorporated herein by reference in their entireties). This PEG-uricase preparation was injected repeatedly into three rabbits in Freund's adjuvant and the rabbits were bled for the preparation of antisera containing polyclonal antibodies against uricase, PEG-uricase conjugates and PEG.

Each rabbit was injected with the PEG-uricase preparation once in complete Freund's adjuvant and five times, at intervals of one to four weeks, in incomplete Freund's adjuvant. Blood was sampled approximately two weeks after each of the last three injections. Serum was prepared from each of the nine blood samples and small volumes of serum were tested for antibodies against PEG by an enzyme-linked-immunosorbent-assay ("ELISA"), using 96-well plates that were coated with mPEG conjugates of a protein that is structurally unrelated to uricase.

Each test bleeding yielded antiserum that reacted with PEG in ELISA analyses. The three rabbits each responded to immunization with PEG with qualitatively similar kinetics and with similar specificity for the methoxyl end group of MPEG, as measured by competitive ELISA. Initially, a dot blot analysis was performed to determine the sensitivity of the anti-PEG antibodies in the rabbit sera. Solutions of PEGs of various sizes and structures and the PEG-uricase solution that was used to immunize the rabbits were spotted onto a polyvinylidene difluoride blotting membrane (Invitrogen, Carlsbad, Calif.; catalog#LS2002). After blocking the membrane with a solution of 2% (w/v) non-fat dry milk powder, the membrane was incubated with a dilution of the rabbit antiserum to PEG-uricase that was prepared as described above. Then a dilution of anti-rabbit IgG antibodies produced in goats and coupled to alkaline phosphatase (Calbiochem, San Diego, Calif.; catalog # 401371) was applied as a secondary antibody. Alkaline phosphatase activity on the blot was detected using a combination of 5-bromo-4-chloro-3-indolyl phosphate and nitroblue tetrazolium (Sigma, catalog # B-1911), as described previously (Blake, M. S., et al. (1984) *Anal Biochem* 136:175-190, the disclosures of which are incorporated herein by reference in their entirety). With high sensitivity and specificity, the rabbit anti-PEG antibodies detected the PEG solutions and the mPEG-protein conjugate that were tested.

Example 2

Demonstration of the Role of the Methoxyl Group in the Antigenicity of mPEG

Unexpectedly, the present inventors have found that the anti-PEG antibodies prepared as described in Example 1 were directed predominantly against the methoxyl end group of the mPEG component of the antigen. FIG. 1 depicts the results from a competitive ELISA assay in which 96-well plates were coated with an mPEG conjugate of a protein that is structurally unrelated to uricase. After blocking the plate with 2% goat serum, solutions of increasing concentration of 4.8-kDa mPEG (Polymer Laboratories, catalog # 6570-5010), 10-kDa mPEG (Union Carbide, catalog # MPEG-10,000) or 10-kDa t-butoxyPEG (Polymer Laboratories, catalog # 29999997) were added and incubated with a 1:1,000 dilution of rabbit antiserum formed against the mPEG-uricase conjugate. After removing the solution, the extent of anti-PEG antibody bound to the mPEG-protein conjugate on the plate was measured spectrophotometrically, using a peroxidase-conjugated secondary antibody (goat anti-rabbit IgG, Calbiochem®, San Diego, Calif.; catalog # 401393) followed by the addition of the peroxidase substrate, o-phenylenediamine dihydrochloride (Sigma, St. Louis, Mo.; catalog # P-9781). For each sample, the initial reaction rate (in milli-absorbance units per minute) observed in the absence of a competitor was designated as 100%. The overlapping curves of the two solutions of mPEG suggest that the length of the PEG backbone is not the predominant determinant of its antigenicity. The curve for t-butoxyPEG is shifted to the right by approximately 2 log units, indicating that t-butoxyPEG has about a 100-fold lower affinity than mPEG for antibodies generated against an mPEG-protein conjugate. In previous unpublished experiments by certain of the present inventors, however, it was found that t-butoxyPEG displays significant immunogenicity when conjugated to an immunogenic protein. Thus, while FIG. 1 demonstrates very little cross-reactivity of t-butoxyPEG with antibodies raised against mPEG, the use of t-butoxyPEG instead of MPEG in the production of PEGylated therapeutic proteins would not solve the problem of the immunogenicity of the PEG component.

Figure 2A:
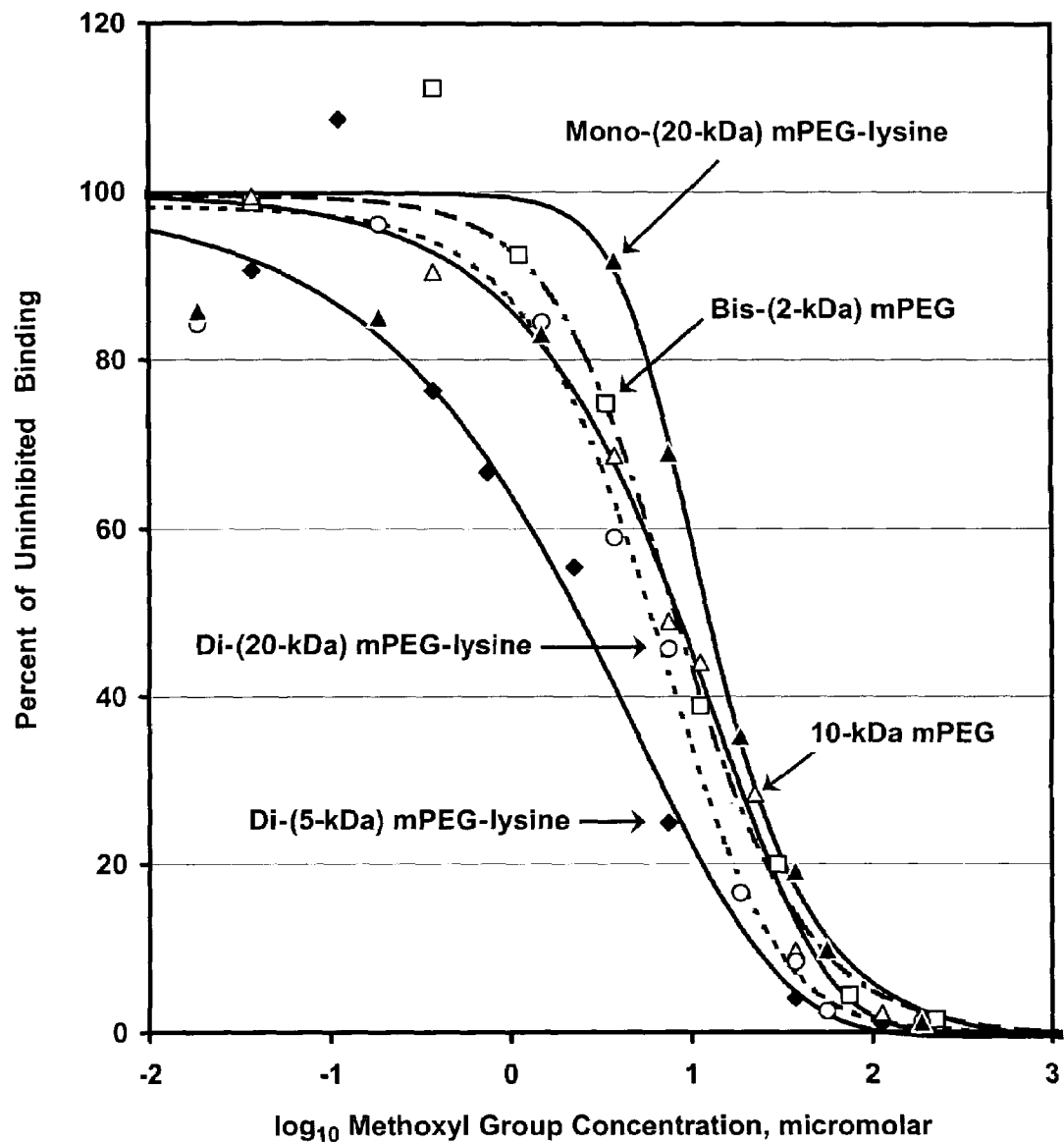
FIG. 2a displays the results from a competitive ELISA, performed as described for FIG. 1, using PEGs of various sizes and structures containing either one or two methoxyl groups. The results for antibody binding are graphed as a function of the molar concentration of methoxyl groups in each sample.

The results depicted in FIG. 1 suggest that the methoxyl group on mPEG is the predominant antigenic group on the polymer molecule. To confirm this inference, the antibodies generated as described in Example 1 were subjected to competitive ELISA analysis, performed as described for FIG. 1, using PEGs of various sizes and structures containing one or two methoxyl groups. FIG. 2a displays the results for antibody binding, graphed as a function of the molar concentration of methoxyl groups in each sample. The concentration of competitor resulting in 50% inhibition of the binding ("$IC_{50}$") was calculated using the equation for a 5-parameter sigmoid curve and the program SigmaPlot®, (SPSS Science, Chicago, Ill.).

Figure 2B:
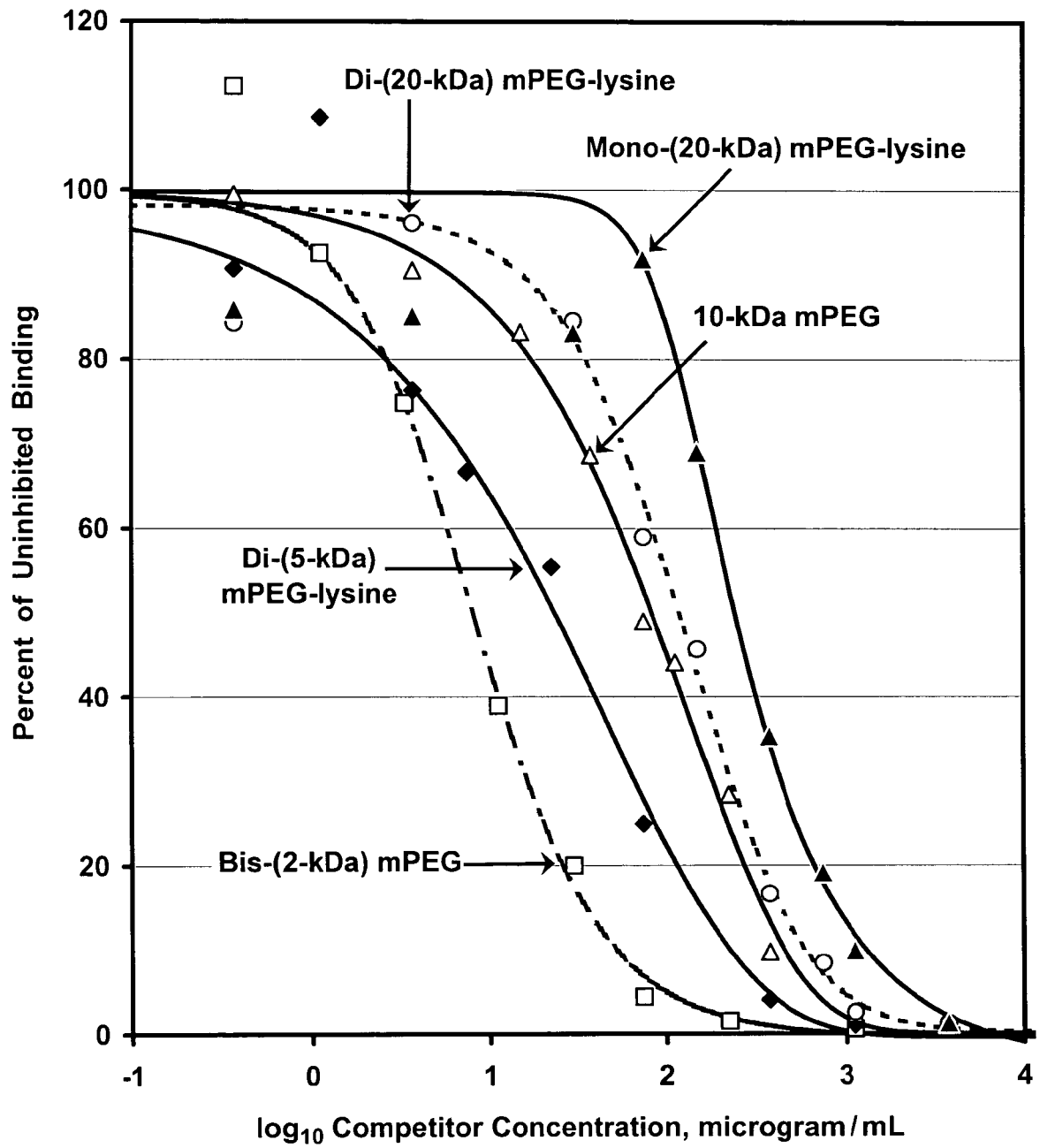
FIG. 2b displays the same data as FIG. 2a, graphed as a function of the weight concentration of PEG (microgram/mL) instead of the molar concentration of methoxyl groups.

As shown in FIG. 2a, the following PEGs were all similarly antigenic on a molar basis: linear PEGs with one methoxyl group ("10-kDa mPEG"), prepared by hydrolysis of mPEG- NPC (PEG-Shop) and "mono-20-kDa mPEG-lysine," synthesized by coupling lysine to 20-kDa NPC-PEG (Shearwater, catalog # M-NPC-20,000); a linear PEG with two methoxyl groups ("Bis-(2-kDa) mPEG" (Sigma-Aldrich, catalog # 81314)), and a large "branched" PEG containing two methoxyl groups ("Di-(20-kDa) mPEG-lysine" (Shearwater, catalog # PEG2-NHS-40K)). In contrast, the curve for the smaller "branched" PEG with two methoxyl groups ("Di-(5-kDa) mPEG-lysine" (Shearwater, catalog # 2Z3X0L01)) was shifted to the left of the mean of the results for the other samples by 0.5 to 0.6 log units, indicating that this form of "branched" mPEG is three to four times as antigenic as the other samples tested in this experiment. FIG. 2b displays the data from FIG. 2a as a function of the weight concentration of mPEG (microgram/mL) instead of the molar concentration of methoxyl groups, supporting the conclusion that it is the methoxyl group that is critical for the interaction of mPEG with the anti-mPEG antibodies.

Figure 3:
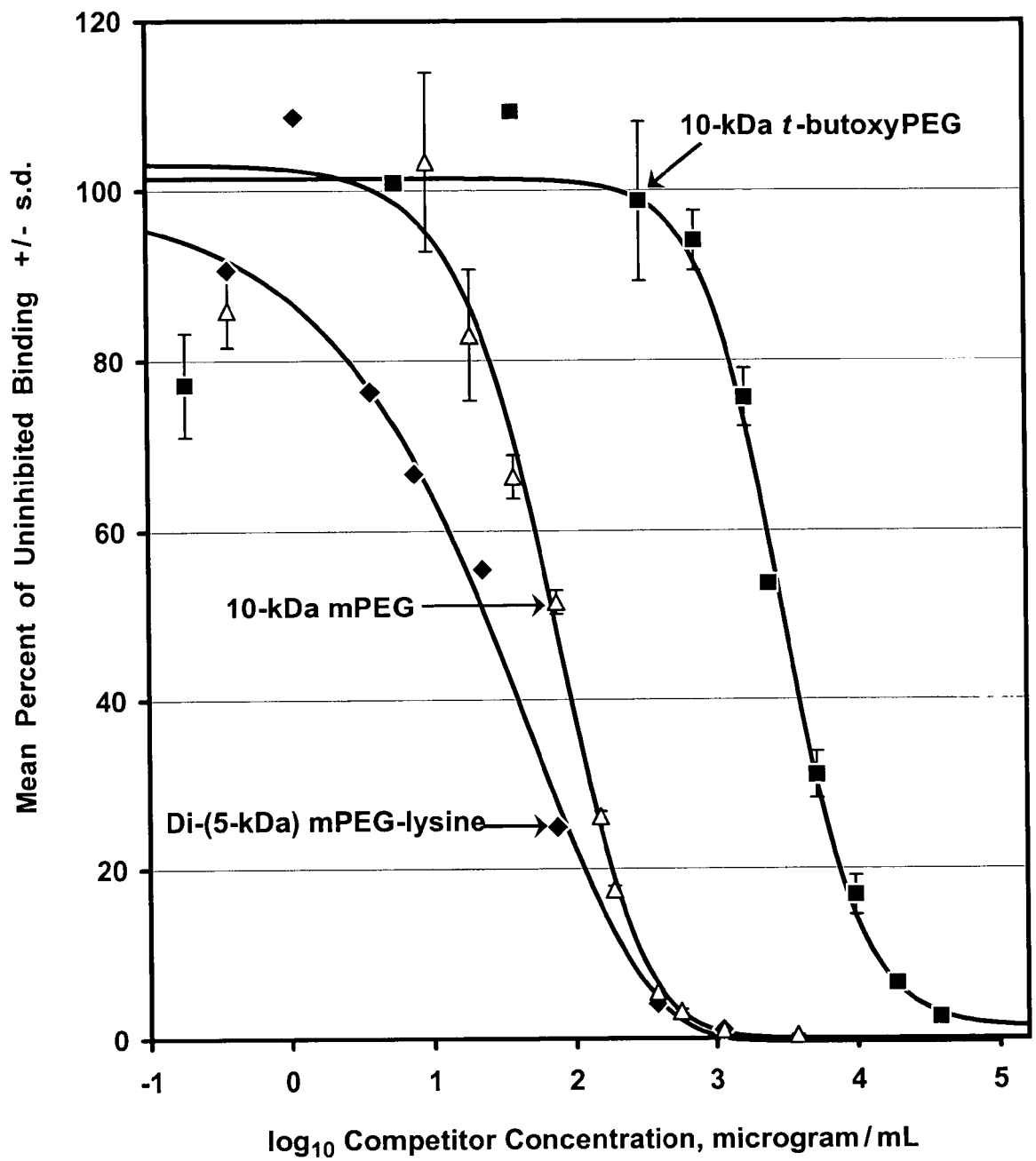
FIG. 3 displays some of the data from FIGS. 1, 2a and 2b in a format that demonstrates the direct dependence of antigenicity on the number of methoxyl groups per molecule of PEG. These samples include 10-kDa PEGs, one of which lacks a methoxyl group (t-butoxyPEG), one that contains one methoxyl group (mPEG) and one that contains two methoxyl groups [Di-(5-kDa) mPEG-lysine].

FIG. 3 displays a subset of the data from FIGS. 1, 2a and 2b in a format that demonstrates the direct dependence of the antigenicity on the number of methoxyl groups per molecule of PEG. These samples represent 10-kDa PEGs with no methoxyl group ("10-kDa t-butoxyPEG"), with one methoxyl group ("10-kDa mPEG") or with two methoxyl groups ("Di (5-kDa) mPEG-lysine"). The results indicate that the antigenicity of a given polymer, and thus of a conjugate of the invention produced with this polymer, is directly dependent upon the number of methoxyl groups contained on the PEG polymer molecule. The larger the number of methoxyl groups, the higher the affinity of the polymer for the antibodies raised against an mPEG-protein conjugate.

Taken together, these results indicate that complete inhibition of the binding of the rabbit antibodies to an mPEG conjugate could be accomplished by competition with solutions of PEG, and especially of mPEG. Moreover, the ability of solutions of mPEGs to block the binding of the rabbit anti-PEG antibodies to mPEG conjugates of an unrelated protein is correlated with their content of methoxyl groups. On the basis of concentration by weight, mPEGs of lower molecular weight were more potent competitors than mPEGs of higher molecular weight, as shown in FIG. 2b. This conclusion is consistent with the fact that the ratio of the mass of the methoxyl groups to the total mass of the polymer decreases as the molecular weight of the polymer increases. Among the PEGs that were tested, the most potent antigens (on a molar basis) were the "branched" PEGs containing two methoxyl groups, which are sometimes referred to as umbrella-like or "U-PEGs" (Martinez, A., et al., U.S. Pat. No. 5,643,575) or as "Y-PEGs" (Greenwald, R. B., et al. published U.S. Patent Application No. 2002/0052443 A1).

Example 3

Testing of Anti-PEG Antibodies with PEGs Lacking Methyoxyl Groups

Figure 4:
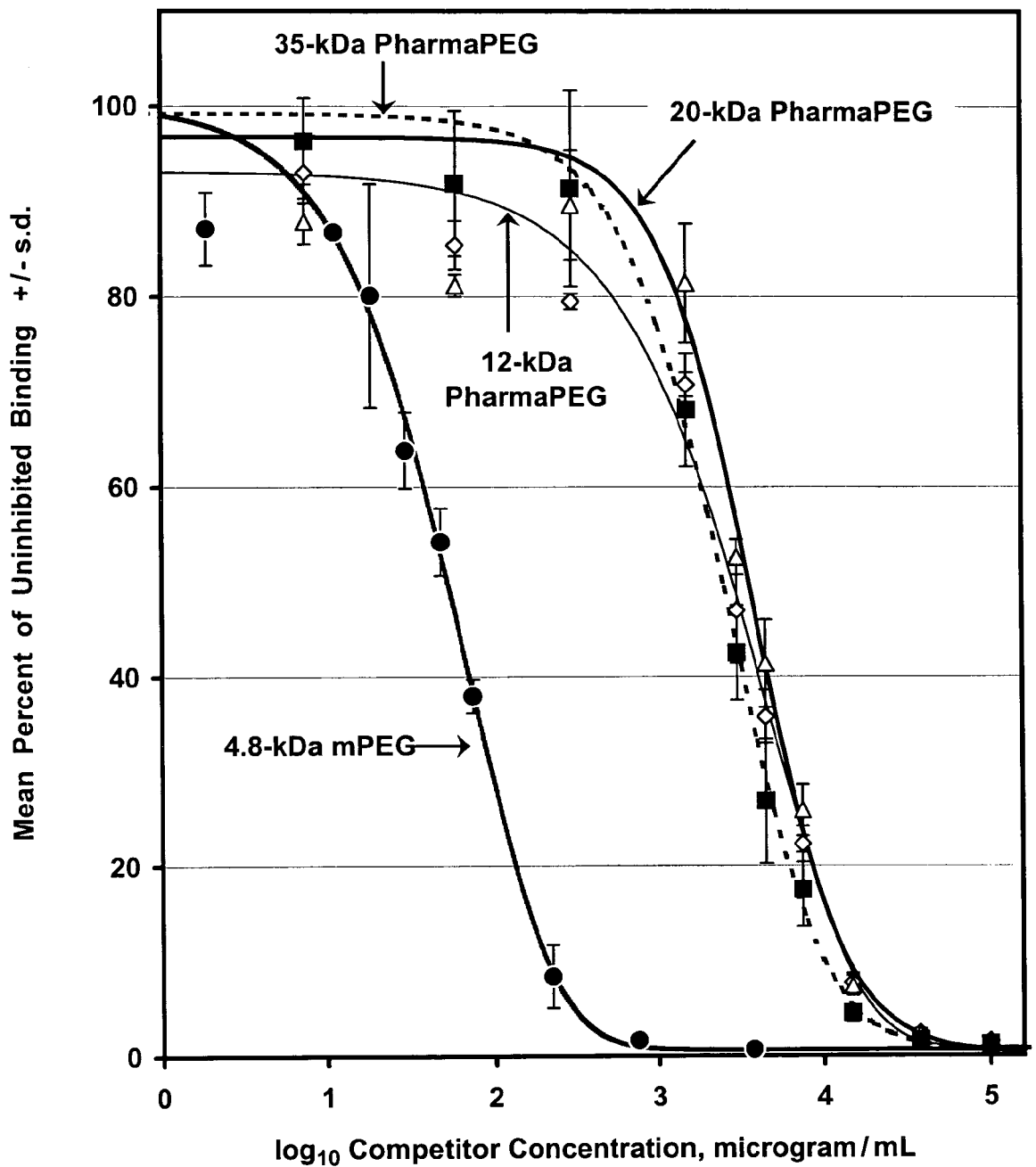
FIG. 4 illustrates a competitive ELISA, as described for FIG. 1, in which 4.8-kDa mPEG is compared with three PEGs of the invention that have no methoxyl groups at the ends of the linear polymer (labeled "PharmaPEG"). The shift between the curves on the horizontal axis indicates that the antigenicities of all three of the PEGs of the invention are approximately 100-fold lower than that of MPEG, when assayed with anti-mPEG antibodies.

The term "PharmaPEG" is used herein to refer to linear or branched PEGs lacking an antigenic group at the terminus or termini that is or are distal from the terminus that is activated or can be activated. From the previous examples, it can be inferred that the antigenicity of a polymer, and therefore of a polymer conjugate of a bioactive agent, is a function of the content of methoxyl groups in the polymer. To further test this inference, competitive ELISA analyses were performed, as described for FIG. 1, comparing the abilities of mPEG ("4.8-kDa mPEG") and 12-kDa, 20-kDa and 35-kDa PharmaPEGs, which have no methoxyl groups or other alkoxyl groups at the ends of the linear polymers, to be bound by anti-mPEG antibodies. Results are shown in FIG. 4. The shift of the three PharmaPEG curves relative to the MPEG curve depicted in FIG. 4 indicates that the antigenicity of PharmaPEG is approximately 100-fold lower than that of mPEG, when assayed with anti-mPEG antibodies. Hence, polymers lacking methoxyl groups (e.g., PharmaPEG) are reduced or substantially reduced in antigenicity when compared to the polymers that are traditionally used for bioconjugation of pharmaceuticals, e.g., MPEG.

As noted above, on a weight basis, the competitive potencies of mPEGs are inversely proportional to their molecular weights. However, PEGs lacking methoxyl groups had only about 1% of the competitive potencies of mPEGs, independent of their molecular weights. These results support the conclusion that monofunctionally reactive polymers lacking methoxyl groups are particularly well suited for use in preparing polymer conjugates of bioactive agents that have reduced, substantially reduced, or no antigenicity compared to conjugates produced using mPEGs, especially "branched" mPEGs, such as di-mPEG-lysine.

Example 4

Figure 5A:
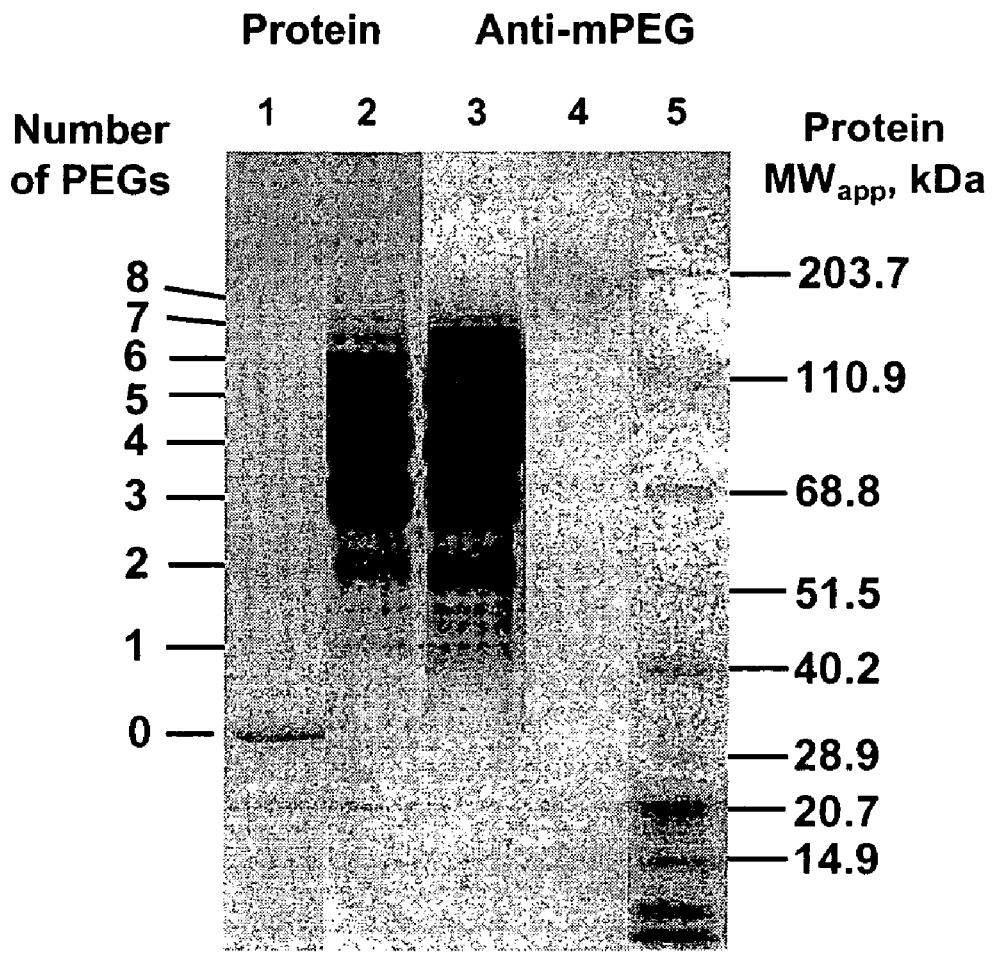
FIG. 5a displays the results of studies in which samples of an isomer of carbonic anhydrase ("CA II") and the same carbonic anhydrase coupled to an average of 3-4 strands of 5-kDa MPEG were analyzed by polyacrylamide gel electrophoresis in the presence of sodium dodecyl sulfate ("SDS-PAGE"). Lanes 1 and 2 of the gel show the results obtained by staining for protein using SYPRO® brand Ruby stain and photography in a dark hood with illumination at 302 nm. Lanes 3 and 4 show the results of a Western blot of the mPEG conjugates and the unPEGylated enzyme, respectively, in which polyclonal rabbit anti-mPEG antibodies were used as the primary antibodies. Lane 5 shows the positions of pre-stained protein standards.

Detection of PEGylated Protein Conjugates by Western Blots with Anti-mPEG Antibodies MonomethoxyPEG conjugates of carbonic anhydrase (EC 4.2.1.1; "CA II") were used as models in testing the ability of the anti-mPEG antibodies to detect PEGylated protein conjugates following polyacrylamide gel electrophoresis in the presence of sodium dodecyl sulfate ("SDS-PAGE"). Gels were electroblotted onto a polyvinylidene difluoride membrane and the blots were incubated with rabbit anti-mPEG antibodies (diluted 1:200), followed by incubation with a secondary antibody (goat anti-rabbit IgG) conjugated to alkaline phosphatase and exposure to a substrate that forms a colored precipitate. This method of immunologic detection of proteins or polymer-protein conjugates transferred from an electrophoretic gel to a membrane is commonly referred to as a "Western blot" (Tsang, V. C. W., et al., (1984) *Anal Biochem* 143:304-307). The detection procedure and reagents were the same as those described for the dot blots in Example 1. The results are shown in FIG. 5a. Lanes 1 and 2 show a gel stained for protein using SYPRO® brand Ruby Stain (Molecular Probes, Eugene, Oreg., catalog # S-12000) and photographed with a Kodak digital camera, using an Orange/Red visible light filter (Molecular Probes, catalog # S-6655) in a dark hood with illumination at 302 nm. Lanes 3 and 4 show the results of a Western blot of the same samples. Anti-mPEG antibodies are seen in the positions of all of the PEGylated species (Lane 3) but not of the unmodified carbonic anhydrase (Lane 4).

Figure 5B:
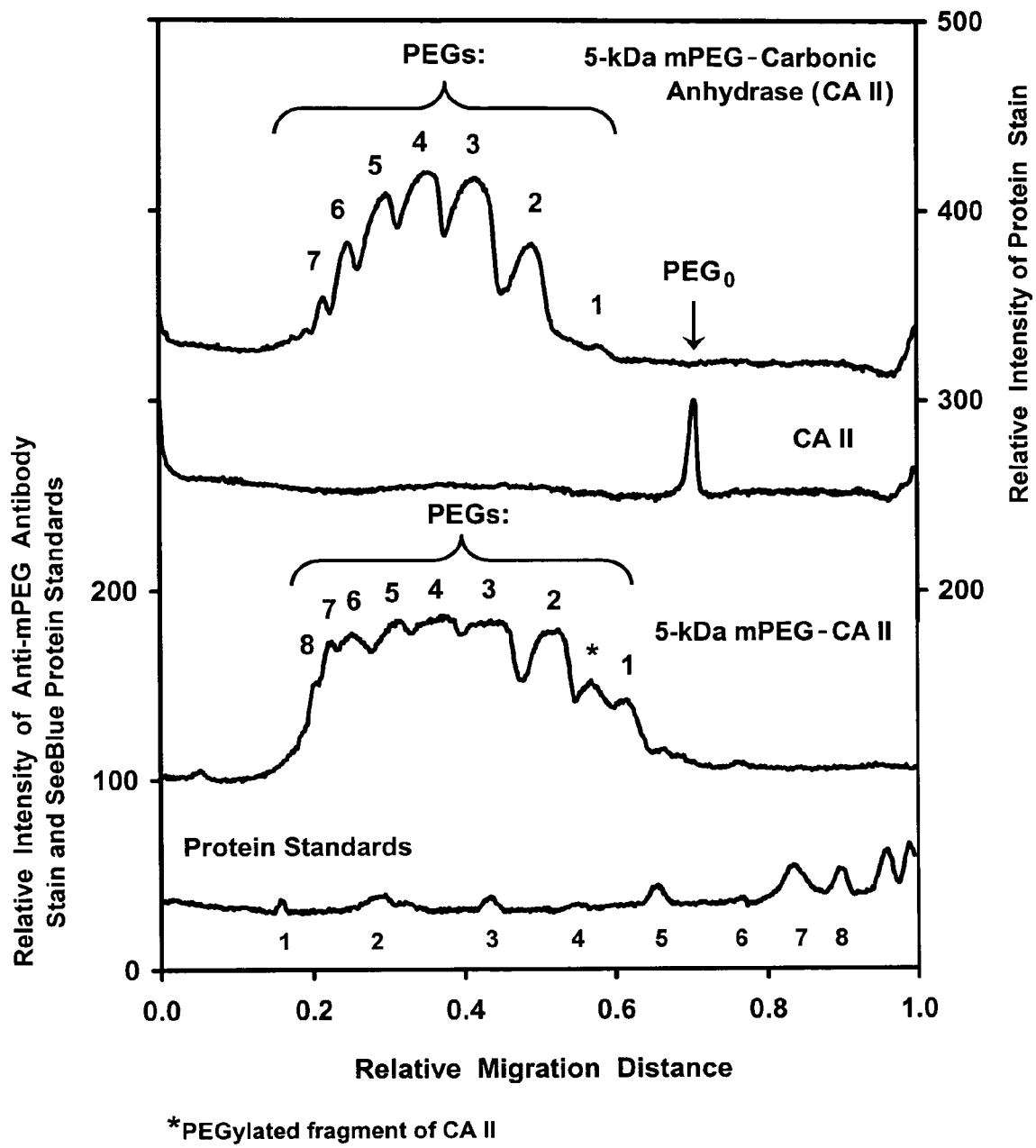
FIG. 5b shows the quantitation of the band intensities in the gel and the Western blot shown in FIG. 5a, obtained with Kodak camera and digital imaging software. The horizontal axis represents the migration distance relative to the dye front and the vertical axis represents the relative intensities of the protein stain or anti-mPEG stain. The bottom tracing shows bands of pre-stained standard proteins with apparent molecular weights, from left to right, of 203.8, 110.9, 68.8, 51.5, 40.2, 28.9, 20.7 and 14.9 kDa. The second tracing from the bottom is an anti-mPEG antibody stain of PEGylated carbonic anhydrase. The third tracing from the bottom represents the protein-stained band of carbonic anhydrase and the top tracing represents the protein-stained bands of the mPEG conjugates of carbonic anhydrase.

FIG. 5b shows the quantitation of band intensities in the gel and Western blot shown in FIG. 5a, obtained with Kodak ID Imaging Analysis software (Kodak, Rochester, N.Y.). The horizontal axis represents the migration distance relative to the dye front and the vertical axis represents the relative intensities of the protein stain or anti-mPEG stain. The bottom tracing shows bands of SeeBlue Plus2™ brand prestained standard proteins (Invitrogen Corporation, Carlsbad, Calif.; catalog # LC5625), in which the peaks numbered 1 through 8 identify proteins with the following apparent molecular weights (in kDa): 204, 111, 68.8, 51.5, 40.2, 28.9, 20.7 and 14.9, respectively. The second tracing from the bottom is an anti-mPEG antibody stain of PEGylated carbonic anhydrase. The third tracing from the bottom represents the protein-stained band of carbonic anhydrase and the top tracing shows the protein-stained mPEG conjugates of carbonic anhydrase. The numbers above the peaks in FIG. 5b indicate the numbers of mPEG strands coupled to carbonic anhydrase in the conjugate(s) in that peak. PEG$_0$ indicates the position of carbonic anhydrase to which no PEG is coupled.

Together, these results indicate that anti-mPEG antibodies are able to form complexes readily with PEGylated proteins prepared with a reactive form of MPEG, and thereby allow their sensitive and selective detection. When such conjugates are introduced into an animal for diagnostic, prophylactic or therapeutic purposes, the induction of anti-mPEG antibodies would contribute to an accelerated rate of clearance of the agent from the bloodstream, thereby limiting the efficacy of those conjugates and potentially leading to adverse effects mediated by the formation of immune complexes.

Example 5

Synthesis of PharmaPEG-Mononitrophenyl Carbonate

A requirement for preparing monofunctionally activated PharmaPEG from PEG diol is that, at some step in the synthesis, one of the terminal groups of the PEG must have properties that allow the separation of PEGs containing different numbers of that terminal group. Such a group might be more hydrophobic than either PEG or activated PEG, allowing the separation by reversed-phase chromatography ("RP chromatography"). Alternatively, such a group might be charged, permitting separation by ion-exchange chromatography. Such a group might be part of a solid phase, allowing phase separation from liquids in which the unbound PEG is soluble. If the activating group can be used as the basis of the separation, as in the case of NPC-PEG described in this Example 5, then the attachment of the activating group is the only synthetic reaction needed. If a removable blocking group, e.g., a t-butyl or triphenylmethyl ("trityl") group, provides the basis of the separation, the blocking group can be added either before or after the attachment of the activated or activatable group, as described in Example 6. In theory, the purification step used to isolate PEG containing the desired number of blocking groups can be performed at any time after the blocking group is attached. In practice, the relative labilities of the bonds between the polymer backbone and the blocking group and between the polymer backbone and the activating (or activatable) group may dictate the optimal sequence of the steps.

The synthesis of monofunctionally activated NPC-PEG from dihydroxyPEG is summarized in the following diagram, in which Ph denotes a phenyl group and n denotes the number of ethylene oxide units in the polymer, which is about 227 for 10-kDa PEG.

HO(CH$_2$CH$_2$O)$_n$H ("PEG Diol")

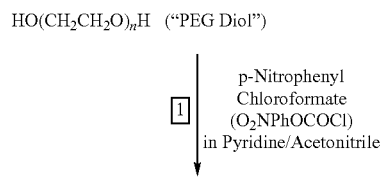

-continued
HO(CH$_2$CH$_2$O)$_n$H + O$_2$NPhOCOO(CH$_2$CH$_2$O)$_n$OCOPhNO$_2$ +

O$_2$NPhOCOO(CH$_2$CH$_2$O)$_n$H

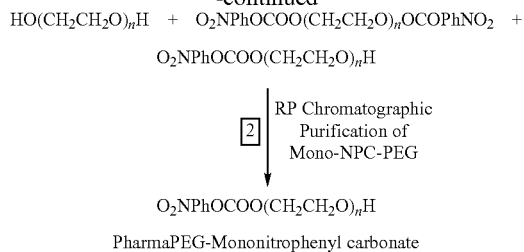

O$_2$NPhOCOO(CH$_2$CH$_2$O)$_n$H

PharmaPEG-Mononitrophenyl carbonate

PEG diols from several suppliers, all of which were labeled as having molecular weights of 10 kDa, were tested for purity and homogeneity. None of them contained more than 90% of PEG with a molecular weight of about 10 kDa. Therefore, 10-kDa PEG diol (Fluka Chemical Corp., Milwaukee, Wis., catalog #81280) was fractionated from contaminants of lower molecular weight by reversed-phase chromatography on an Amberchrom MD-P CG-300SD column (7.5 mm×15 cm, TosoHaas, Montgomeryville, Pa.). PEG was loaded onto the column as a solution in 5% (v/v) acetonitrile in water and was eluted with a linear gradient of 5% to 35% acetonitrile in water. Fractions were analyzed by size-exclusion chromatography on a Superdex® 200 brand HR10/30 column (Amersham Pharmacia Biotech, Piscataway, N.J.) in 20 mM sodium acetate containing 150 mM NaCl, pH 4.6. Fractions from the Amberchrom column in which more than 98% of the refractive index ("RI") signal due to PEG was in the peak corresponding to about 10-kDa PEG were pooled and lyophilized.

The purified, dried PEG diol (530 mg) was combined with 61.4 mg p-nitrophenyl chloroformate (Aldrich, Milwaukee, Wis., catalog # 16,021-0) and dissolved in 4 mL acetonitrile in a screw-capped 13×100 mm glass tube, giving final concentrations of about 12.5 mM PEG diol and about 75 mM p-nitrophenyl chloroformate. Pyridine (0.25 g) was added and the reaction mixture was incubated overnight at 36° C. The reaction was quenched by stirring the mixture into 33 mL of ice-cold 0.1 M hydrochloric acid. The solution was filtered to remove a slight precipitate of p-nitrophenol and was dialyzed for one day in the cold against four 1-L changes of water. Acetonitrile was added to the dialyzed solution to bring the concentration to 5% (v/v). Half of the mixture produced in Step 1 (24 mL), which contained about 265 mg of the purified 10-kDa PEG diol, was loaded onto the Amberchrom column and the bound PEG species were eluted with a gradient of 5% to 65% acetonitrile in water. Fractions were analyzed by size-exclusion chromatography as before, monitoring both the refractive index and absorbance at 280 nm. Dihydroxy-PEG, which lacked absorbance at 280 nm, was eluted first, followed by PEG derivatized with a single p-nitrophenyl group ("mono-NPC PEG"), followed by di-NPC PEG, for which the ratio of absorbance at 280 nm to the refractive index was twice that of mono-NPC-PEG. Two fractions in the center of the mono-NPC PEG elution range were combined to give about 110 mg of mono-NPC PEG, corresponding to a yield of about 42%. The product of Step 2 could be dried for storage in a desiccator and/or a freezer or used directly for coupling to an amine-containing bioactive compound or to a linker containing two or more amino groups for the preparation of branched PEGs, e.g., diPEG-lysine, which contained no alkoxyl groups.

Example 6

Synthesis of a PharmaPEG-Monoaldehyde from PEG Diol

The synthesis of the monopropionaldehyde derivative of PharmaPEG is summarized in the following diagram, in which KOtBu denotes potassium t-butoxide, and DEP denotes the 3,3-diethoxypropyl group.

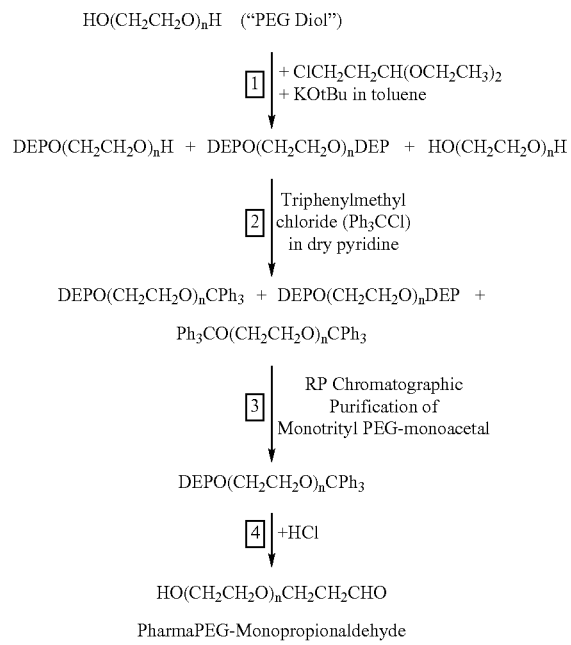

Preferably, the dihydroxyPEG that is used as starting material for Step 1 will have a molecular weight that is within 10% of its nominal molecular weight and will have a polydispersity of <1.05. Polydispersity is defined as the ratio of the weight-average molecular weight ("$M_w$") to the number-average molecular weight ("$M_n$"). Both of these parameters, $M_w$ and $M_n$, can be measured by size-exclusion chromatography, using PEGs of accurately known molecular weights as standards and gel permeation chromatography software such as EZChrom Elite Client/Server Software, Version 2.8.3 (Scientific Software, Inc., Pleasanton, Calif.). Alternatively, the polydispersity of PEGs can be measured by matrix-assisted laser desorption/ionization time-of-flight ("MALDI-TOF") mass spectroscopy (Marie, A., et al., (2000) Anal Chem 72:5106-5114), using software such as Voyager Software (Applied Biosystems, Foster City, Calif.). For the preparation of pharmaceutical products containing covalently linked PEG, the PEG starting material will preferably have a polydispersity of <1.02, and more preferably <1.01, when measured by MALDI-TOF mass spectroscopy. The starting material may be obtained from Aldrich Chemical Co., Fluka Chemicals (Buchs, Switzerland), Shearwater Corporation or from Sigma Chemical Co., among other suppliers that are known to those skilled in the art. If the starting material is not sufficiently homogeneous, it can be fractionated by an adaptation of the method described in Example 5.

A mixture of monopropionaldehyde and dipropionaldehyde diethyl acetal derivatives of PEG diol can be synthesized using 3-chloro-propionaldehyde diethyl acetal (Aldrich catalog #C6,900-4), as described for acetaldehyde diethyl acetal by Harris, J. M., et al., ((1984) J Polym Sci 22:341-352) (see Step 1). Similar methods were also described by Bentley, M. D., et al., ((1998) J Pharm Sci 87:1446-1449) and were subsequently patented by Bentley, M. D., et al. (U.S. Pat. No. 5,990,237).

A sufficient quantity of triphenylmethyl chloride (chlorotriphenyl-methane or trityl chloride, $Ph_3CCl$, e.g., Aldrich catalog # T8,380-1) dissolved in pyridine is added to the mixture produced in Step 1 so that, under the reaction conditions, the $Ph_3CCl$ will react with all of the hydroxyl groups of the PEG starting material that are not coupled to the propionaldehyde diethyl acetal (Kocienski, P. J., supra). To complete Step 2, the mixture is recovered after precipitation by the addition of a poor solvent for PEG (e.g., ether) or by evaporation of the solvent or by other methods that are known in the art.

The mixture recovered from Step 2 is dissolved in water before or after the addition of 5% (v/v) acetonitrile and the solution is loaded onto a reversed-phase column that is expected from principles known in the art to be capable of binding trityl derivatives of PEG. The column may contain alkyl or aryl derivatives of silica or a polymeric substrate, or it may be a styrene-based polymer (e.g., Amberchrom MD-P CG-300), as in Example 5. The PEG diol and trityl derivatives can be eluted in a reversed-phase mode with an increasing gradient of organic solvent, as in Example 5, or in a sample displacement mode by continuing to load the column until at least a portion of the desired species has been eluted (Agner, E., et al., PCT publication WO 00/23798 A1) (or in displacement mode (Cramer, S. M., U.S. Pat. No. 6,239,262), or in a combination of these modes. In general, the PEG derivative lacking any trityl group will elute first, the monotrityl derivative will elute second and the ditrityl PEG will elute third. An optimal yield of the desired product is obtained when the ratios of these three species are 1:2:1. To improve the yield and/or purity of the desired monotrityl PEG product, it may be desirable to subject a portion of the column effluent to recycling chromatography, as is well known in the chromatographic art. To complete Step 3, the portion of the eluate that contains at least a portion of the monotrityl derivative is separated, concentrated and dried by methods that are known in the art.

Under mildly acidic conditions and at low temperature, the acetal can be converted to the aldehyde, while preserving most of the trityl linkage at the distal end of the PEG. In some applications of this example, it may be advantageous to react the monotrityl PEG monoaldehyde with a target moiety before removing the trityl group. Such embodiments are envisioned by and included in the present invention.

Example 7

Figure 6A:
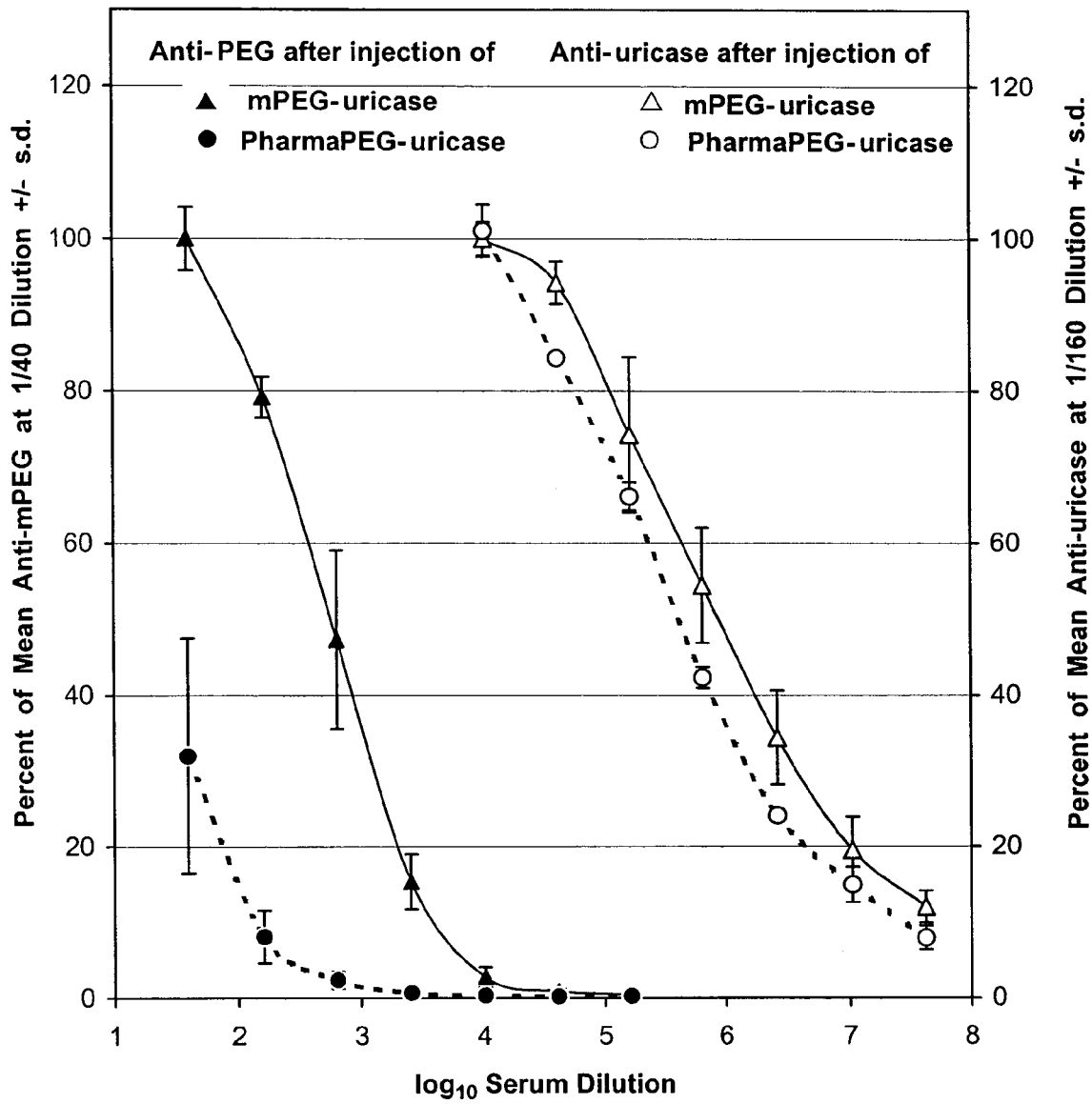
FIGS. 6a and 6b show the results of ELISA analyses of sera from groups of three rabbits that were immunized with conjugates of porcine uricase containing an average of about two strands of either mPEG or hydroxyPEG ("PharmaPEG") per uricase subunit. Antibodies against uricase were measured using assay plates coated with porcine uricase. Antibodies against PEG were measured using plates coated with conjugates of an unrelated protein coupled to mPEG.
Figure 6B:
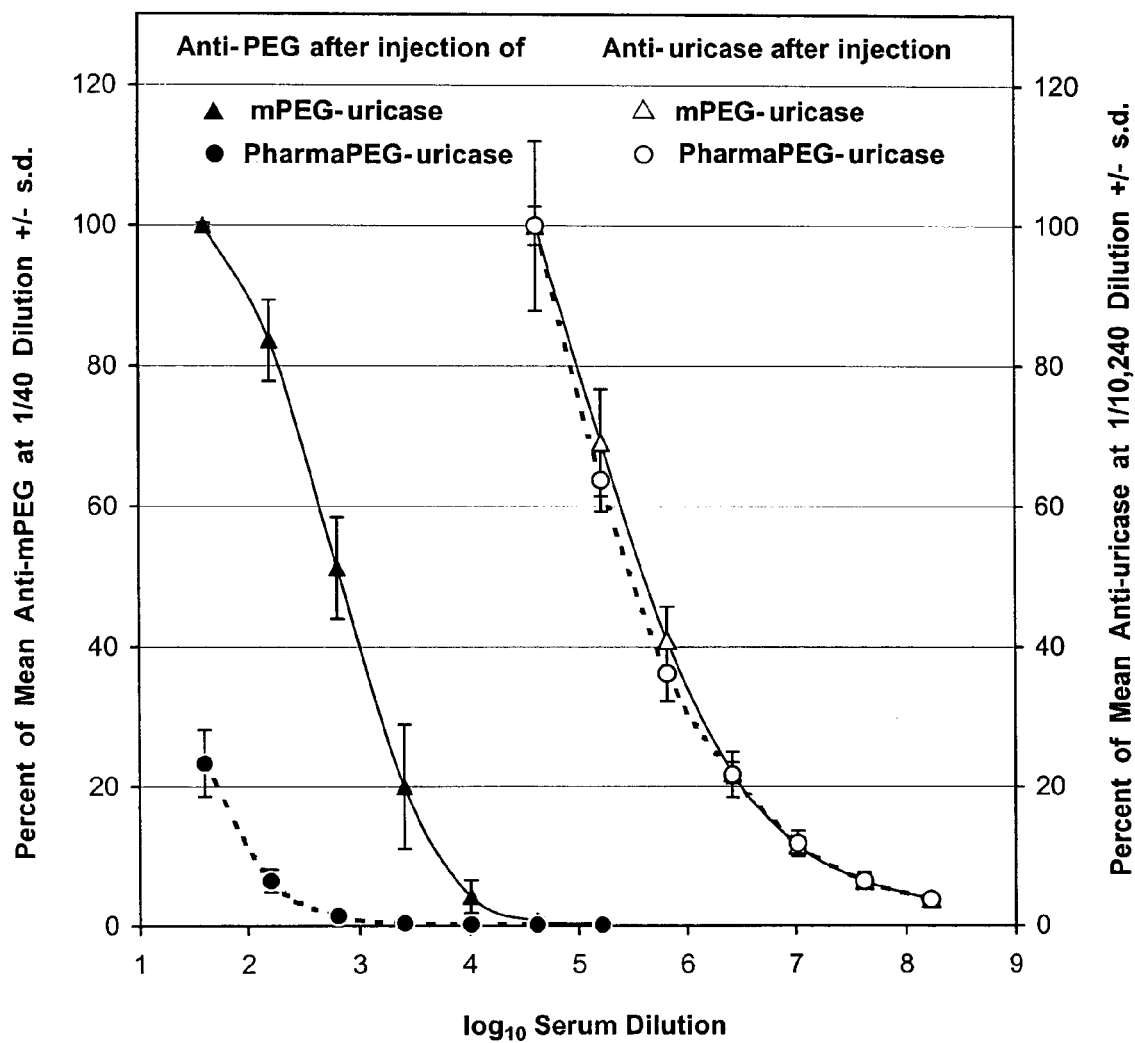

Demonstration of the Decreased Immunogenicity of Conjugates Prepared with HydroxyPEG Compared with MethoxyPEG Proceeding as described for immunization with mPEG conjugates of uricase, as in Example 1, groups of three rabbits were immunized with either MPEG conjugates or hydroxyPEG conjugates of the same preparation of porcine uricase, each containing an average of about two strands of 10-kDa PEG per uricase subunit. The average number of strands of polymer attached to each preparation of conjugates was confirmed by both size-exclusion HPLC analyses and by SDS-PAGE, in which the gels were stained both for protein, as in Example 4, and for PEG, using the method described in commonly owned co-pending U.S. patent application Ser. No. 10/183,607, filed Jun. 28, 2002, which is incorporated herein by reference in its entirety. Each rabbit was injected with one of the PEG-uricase preparations once in complete Freund's adjuvant and five times, at intervals of one to four weeks, in incomplete Freund's adjuvant. Blood was drawn two weeks after the fourth and fifth injections in incomplete Freund's adjuvant and sera were prepared. When serial 4-fold dilutions of the sera from these rabbits were tested by ELISA analyses, as in Example 2, the concentration of anti-PEG antibodies that was induced by the conjugates prepared with hydroxyPEG was found to be less than 5% of that induced by the conjugates prepared with mPEG (see FIGS. 6a and 6b). In contrast, the induction of anti-uricase antibodies by the conjugates prepared with the two types of PEG was similar in the two groups of rabbits. None of the preimmunization sera from these rabbits contained detectable anti-PEG antibodies.

DISCUSSION AND CONCLUSIONS

It has been reported in the art that PEG terminated in a methoxyl group (MPEG) and PEG terminated in a hydroxyl group (bis-hydroxyPEG or PEG diol) are equivalent for use in bioconjugation, or, more often, that mPEGs and other lower alkoxyl PEGs are superior to PEG diols. Moreover, bis-activated diols can act as cross-linking agents, which can be undesirable for producing soluble, long-acting bioconjugates of low immunogenicity and antigenicity. Surprisingly, the results of the present studies indicate that mPEGs are significantly antigenic, and that antibodies induced against the methoxyl group of mPEG bind to PEGylated protein conjugates prepared using mPEG. Hence, unexpectedly and contrary to previous reports, mPEG is not equivalent to hydroxyPEG and mPEG is not preferred for preparing polymer conjugates of bioactive components (such as proteins) that are intended to have increased bioavailability, stability in the blood circulation and minimal immunogenicity.

Based on the present results, it is clear that the use of monofunctionally activated PEG that does not contain a methoxyl group or another alkoxyl group for the synthesis of protein conjugates results in conjugates with decreased immunoreactivity. The resultant conjugates have been demonstrated to have decreased antigenicity, i.e., decreased ability to interact with antibodies developed against mPEG conjugates of the same protein, and decreased immunogenicity, i.e., decreased ability to evoke an immune response against the PEG component. As a corollary, conjugates prepared with branched PEGs containing two or more methoxyl groups are expected to be more immunogenic than conjugates prepared from branched PEGs lacking alkoxyl groups.

Finally, based on the present findings, the use of monofunctionally activated PEG that does not contain a methoxyl group or another alkoxyl group, rather than monofunctionally activated mPEG, for the synthesis of PEG-liposomes is expected to confer on the resulting PEG-liposomes a decreased immunoreactivity, including a decreased tendency to trigger the activation of complement in blood, and a decreased tendency to induce acute respiratory distress or anaphylactoid and pseudo-allergic reactions.

This invention is described herein with reference to certain embodiments thereof. The methods of this invention are similarly applicable to other types of proteins, to other bioactive agents and to other conjugation reagents. Therefore, the scope of this invention is not limited to the embodiments described, but is limited only by the scope of the claims and/or equivalents thereof. Workers of ordinary skill in the art can readily appreciate that other embodiments can be practiced without departing from the scope of this invention. All such variations are considered to be part of this invention.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A composition comprising a conjugate 95% or more pure, said conjugate comprising a peptide, protein or glycoprotein covalently attached to at least one linear or branched polyalkylene glycol(s),
   wherein said linear or branched polyalkylene glycol(s) is or are attached to said peptide, protein or glycoprotein at a single site on said linear or branched polyalkylene glycol(s),
   wherein a hydroxyl group is present on all of the distal polyalkylene glycol termini in said pure conjugate, and
   wherein said pure conjugate exhibits reduced antigenicity compared to a second conjugate comprising the same peptide, protein or glycoprotein linked at the same site or sites on the peptide, protein or glycoprotein to the same number of polyalkylene glycol(s) of the same size and the same linear or branched structure, wherein an alkoxyl or an aryloxyl group is present on the distal polyalkylene glycol termini in said second conjugate.

2. The composition of claim 1, wherein each of said linear or branched polyalkylene glycol(s) is selected from the group consisting of a poly(ethylene glycol) and a copolymer of ethylene oxide and propylene oxide.

3. The composition of claim 2, wherein each of said linear or branched polyalkylene glycol(s) is a poly(ethylene glycol) ("PEG").

4. The composition of claim 3, wherein the attachment of said PEG to said peptide, protein or glycoprotein is carried out using a monofunctionally activated derivative of at least one PEG selected from the group consisting of a linear dihydroxyPEG, a hydroxyPEG-monoacetal and a hydroxyPEG-monoacid.

5. The composition of claim 3, wherein the attachment of said PEG to said peptide, protein or glycoprotein is carried out using a monofunctionally activated derivative of hydroxyPEG selected from the group consisting of a monoaldehyde, a monoester of a monoacid, a monoamine, a monothiol, a monodisulfide, a monobromophenyl carbonate, a monochlorophenyl carbonate, a monofluorophenyl carbonate, a mononitrophenyl carbonate, a monocarbonylimidazole, a monohydrazide, a monocarbazate, a monoiodoacetamide, a monomaleimide, a monoorthopyridyl disulfide, a monooxime, a monophenyl glyoxal, a monothiazolidine-2-thione, a monothioester, a monotriazine and a monovinylsulfone.

6. The composition of claim 1, wherein each of said linear or branched polyalkylene glycol(s) has a molecular weight of from about 1,000 Daltons (1 kDa) to about 100,000 Daltons (100 kDa).

7. The composition of claim 6, wherein each of said linear or branched polyalkylene glycol(s) has two branches, each with a molecular weight of from about 2 kDa to about 30 kDa.

8. The composition of claim 7, wherein each of said linear or branched polyalkylene glycol(s) has two branches, each with a molecular weight of from about 5 kDa to about 20 kDa.

9. The composition of claim 6, wherein each of said linear or branched polyalkylene glycol(s) has a molecular weight of from about 10 kDa to about 20 kDa.

10. The composition of claim 9, wherein each of said linear or branched polyalkylene glycol(s) has a molecular weight of about 12 kDa.

11. The composition of claim 6, wherein each of said linear or branched polyalkylene glycol(s) has a molecular weight of from about 18 kDa to about 60 kDa.

12. The composition of claim 11, wherein each of said linear or branched polyalkylene glycol(s) has a molecular weight of from about 18 kDa to about 22 kDa.

13. The composition of claim 12 wherein each of said linear or branched polyalkylene glycol(s) has a molecular weight of about 20 kDa.

14. The composition of claim 11, wherein each of said linear or branched polyalkylene glycol(s) has a molecular weight of about 27 kDa to about 33 kDa.

15. The composition of claim 1, wherein said peptide, protein or glycoprotein is attached to from one to about 100 molecules of said linear or branched polyalkylene glycol(s).

16. The composition of claim 15, wherein said peptide, protein or glycoprotein is attached to from one to about five molecules of said linear or branched polyalkylene glycol(s).

17. The composition of claim 16, wherein said peptide, protein or glycoprotein is attached to one or two molecules of said linear or branched polyalkylene glycol(s).

18. The conjugate of claim 15, wherein said peptide, protein or glycoprotein is attached to about five to about 100 molecules of said linear or branched polyalkylene glycol(s).

19. The composition of claim 1, wherein each of said linear or branched polyalkylene glycol(s) is selected from the group consisting of a monohydroxyPEG-acid and a di(hydroxyPEG)-acid.

20. The composition of claim 4, wherein the attachment of said PEG to said peptide, protein or glycoprotein is carried out using said monofunctionally activated derivative of said linear dihydroxyPEG.

21. The composition of claim 4, wherein the attachment of said PEG to said peptide, protein or glycoprotein is carried out using said monofunctionally activated derivative of said hydroxyPEG-monoacid.

22. The composition of claim 1, wherein said peptide, protein or glycoprotein is an allergen.

23. The composition of claim 1, wherein said composition is a pharmacuatical composition comprising a pharmaceutically acceptable excipient or carrier.

24. The composition of claim 1, wherein said peptide, protein or glycoprotein is covalently attached to at least one linear or branched polyalkylene glycol that had been converted to a monofunctionally activated polyalkylene glycol by a method comprising:
 (a) obtaining a polyalkylene glycol that has a hydroxyl group at every terminus;
 (b) prior to the conversion of the polyalkylene glycol of (a) to a monofunctionally activated polyalkylene glycol, protecting all except one of the hydroxyl groups in said polyalkylene glycol by the addition of one or more removable blocking groups to obtain a protected monohydroxy polyalkylene glycol;
 (c) producing a monofunctionally activated derivative of said protected polyalkylene glycol of (b) by reacting said protected polyalkylene glycol of (b) with a derivatizing compound or compounds under conditions such that said protected polyalkylene glycol of (b) is derivatized with a single derivatizing group at a hydroxyl group that does not contain said removable blocking group or groups of (b);
 (d) purifying said monofunctionally activated derivative of (c);
 (e) removing said blocking group or groups of (b) from said monofunctionally activated derivative of (d) without removing the derivatizing group attached in (c), to produce a monofunctionally activated polyalkylene glycol wherein the distal terminus or distal termini are hydroxyl group(s); and
 (f) contacting said monofunctionally activated polyalkylene glycol of (e) with said peptide, protein or glycoprotein under conditions that favor the covalent attachment of said monofunctionally activated polyalkylene glycol to said peptide, protein or glycoprotein.

25. The composition of claim 24, wherein each of said linear or branched polyalkylene glycol(s) is selected from the group consisting of a poly(ethylene glycol) and a copolymer of ethylene oxide and propylene oxide.

26. The composition of claim 24, wherein each of said linear or branched polyalkylene glycol(s) is selected from the group consisting of a linear poly(ethylene glycol) and a branched poly(ethylene glycol).

27. The composition of claim 24, wherein each of said linear or branched polyalkylene glycol(s) has a molecular weight of from about 1 kDa to about 100 kDa.

28. The composition of claim 27, wherein each of said linear or branched polyalkylene glycol(s) has two branches, each with a molecular weight of from about 2 kDa to about 30 kDa.

29. The composition of claim 27, wherein each of said linear or branched polyalkylene glycol(s) has a molecular weight of from about 10 kDa to about 20 kDa.

30. The composition of claim 24, wherein said peptide, protein or glycoprotein is attached to from one to about 100 molecules of said linear or branched polyalkylene glycol(s).

31. The composition of claim 30, wherein said peptide, protein or glycoprotein is attached to from one to about five molecules of said linear or branched polyalkylene glycol(s).

32. The composition of claim 31, wherein said peptide, protein or glycoprotein is attached to one or two molecules of said linear or branched polyalkylene glycol(s).

33. The composition of claim 30, wherein said peptide, protein or glycoprotein is attached to about five to about 100 moleculed of said linear or branched polyalkylene glycol(s).

34. The conjugate of claim 24, wherein said monofunctionally activated polyalkylene glycol of (e) is selected from the group consisting of a hydroxyPEG-monoaldehyde and a reactive ester of a hydroxyPEG-monoacid.

35. The composition of claim 24, wherein said monofunctionally activated polyalkylene glycol is derived from a linear dihydroxyPEG.

36. The composition of claim 24, wherein said peptide, protein or glycoprotein is an allergen.

37. A kit comprising more than one container, at least one of said containers comprising the composition of claim 1.

38. The composition of claim 19, wherein each of said linear or branched polyalkylene glycol(s) is di(hydroxyPEG)-lysine.

39. The composition of claim 1, wherein said peptide or protein or glycoprotein is selected from the group consisting of an enzyme, a serum protein, a serum glycoprotein, a blood cell protein, a pigmentary protein, hemoglobin, a viral protein, a peptide hormone, a protein hormone, a glycoprotein hormone, a hypothalamic releasing factor, a cytokine and a growth factor.

40. The composition of claim 39, wherein said peptide, protein or glycoprotein is a serum protein and is selected from the group consisting of an albumin, an immunoglobulin and a blood clotting factor.

41. The composition of claim 39, wherein said peptide, protein or glycoprotein is a peptide hormone or protein hormone or glycoprotein hormone and is selected from the group consisting of an antidiuretic hormone, chorionic gonadotropin, luteinizing hormone, follicle-stimulating hormone, insulin, prolactin, a somatomedin, growth hormone, thyroid-stimulating hormone and a placental lactogen.

42. The composition of claim 39, wherein said peptide, protein or glycoprotein is a growth growth factor and is selected from the group consisting of a colony-stimulating factor, an epidermal growth factor, an erythropoietin, a fibroblast growth factor, an insulin-like growth factor, a transforming growth factor, a platelet-derived growth factor, a nerve growth factor, a hepatocyte growth factor, a neurotrophic factor, a ciliary neurotrophic factor, a brain-derived neurotrophic factor, a glial-derived neurotrophic factor and a bone morphogenic peptide.

43. The composition of claim 39, wherein said peptide, protein or glycoprotein is a cytokine and is selected from the group consisting of a lymphokine, an interleukin, an interferon, a tumor necrosis factor, a leukemia inhibitory factor and thrombopoietin.

44. The composition of claim 39, wherein said peptide, protein or glycoprotein is an enzyme and is selected from the group consisting of a carbohydrate-specific enzyme, a proteolytic enzyme, an oxidoreductase, a transferase, a hydrolase, a lyase, an isomerase and a ligase.

45. The composition of claim 44, wherein said enzyme is a uricase.

46. The composition of claim 44, wherein said enzyme is a plasminogen activator.

47. The composition of claim 24, wherein said peptide, protein or glycoprotein is selected from the group consisting of an enzyme, a serum protein, a serum glycoprotein, a blood cell protein, a pigmentary protein, hemoglobin, a viral protein, a peptide hormone, a protein hormone, a glycoprotein hormone, a hypothalamic releasing factor, a cytokine and a growth factor.

48. The composition of claim 47, wherein said peptide, protein or glycoprotein is a serum protein and is selected from the group consisting of an albumin, an immunoglobulin and a blood-clotting factor.

49. The composition of claim 47, wherein said peptide, protein or glycoprotein is a peptide hormone or protein hormone or glycoprotein hormone and is selected from the group consisting of an antidiuretic hormone, chorionic gonadotropin, luteinizing hormone, follicle-stimulating hormone, insulin, prolactin, a somatomedin, growth hormone, thyroid-stimulating hormone and a placental lactogen.

50. The composition of claim 47, wherein said peptide, protein or glycoprotein is a growth factor and is selected from the group consisting of a colony-stimulating factor, an epidermal growth factor, an erythropoietin, a fibroblast growth factor, an insulin-like growth factor, a transforming growth factor, a platelet-derived growth factor, a nerve growth factor, a hepatocyte growth factor, a neurotrophic factor, a ciliary neurotrophic factor, a brain-derived neurotrophic factor, a glial-derived neurotrophic factor and a bone morphogenic peptide.

51. The composition of claim 47, wherein said peptide, protein or glycoprotein is a cytokine and is selected from the group consisting of a lymphokine, an interleukin, an interferon, a tumor necrosis factor, a leukemia inhibitory factor and thrombopoietin.

52. The composition of claim 47, wherein said peptide, protein or glycoprotein is an enzyme and is selected from the group consisting of a carbohydrate-specific enzyme, a proteolytic enzyme, an oxidoreductase, a transferase, a hydrolase, a lyase, an isomerase and a ligase.

53. The composition of claim 52, wherein said enzyme is a uricase.

54. The composition of claim 52, wherein said enzyme is a plasminogen activator.

55. The composition of claim 39, wherein said peptide, protein or glycoprotein is a colony-stimulating factor.

56. The composition of claim 55, wherein said colony-stimulating factor is a granulocyte-macrophage colony-stimulating factor (GM-CSF).

57. The composition of claim 56, wherein said GM-CSF is covalently attached to one linear or branched polyalkylene glycol molecule.

58. The composition of claim 56, wherein said GM-CSF is covalently attached to two linear or branched polyalkylene glycol molecules.

59. The composition of claim 47, wherein said peptide, protein or glycoprotein is a colony-stimulating factor.

60. The composition of claim 59, wherein said colony-stimulating factor is a GM-CSF.

61. The composition of claim 42, wherein said peptide, protein or glycoprotein is an erythropoietin.

62. The composition of claim 50, wherein said peptide, protein or glycoprotein is an erythropoietin.

63. The composition of claim 16, wherein said peptide, protein or glycoprotein is attached to from one to three molecules of said linear or branched polyalkylene glycol(s).

64. The composition of claim 24, wherein said peptide, protein or glycoprotein is attached to from one to three molecules of said linear or branched polyalkylene glycol(s).

65. The composition of claim 1, wherein said pure conjugate is 98% or more pure.

66. The composition of claim 1, wherein said pure conjugate is 99% or more pure.

67. The composition of claim 24, wherein said one or more removable blocking groups is or are selected from the group consisting of t-butoxyl groups, aryloxyl groups, and triphenylmethyl groups.

68. The composition of claim 24, wherein said contacting (f) is performed prior to said removing (e).

69. The composition of claim 1, wherein said peptide, protein or glycoprotein is covalently attached to at least one linear or branched polyalkylene glycol that had been activated at only one terminus produced by a method comprising:
  obtaining a polyalkylene glycol that has a hydroxyl group at every terminus;
  producing a monofunctionally activated derivative of said polyalkylene glycol of (a) by reacting said polyalkylene glycol of (a) with a derivatizing compound or compounds under conditions such that a monofunctionally activated derivative of said polyalkylene glycol of (a) is formed;
  (c) purifying said monofunctionally activated derivative of (b); and
  (d) contacting said purified monofunctionally activated derivative of (c) with said peptide, protein or glycoprotein under conditions that favor the covalent attachment of said purified monofunctionally activated derivative of (c) to said peptide, protein or glycoprotein.

70. The composition of claim 69, wherein said polyalkylene glycol of (a) is selected from the group consisting of a poly(ethylene glycol) and a copolymer of ethylene oxide and propylene oxide.

71. The composition of claim 69, wherein said polyalkylene glycol of (a) is selected from the group consisting of a linear poly(ethylene glycol) and a branched poly(ethylene glycol).

72. The composition of claim 69, wherein each said polyalkylene glycol of (a) has a molecular weight of from about 1 kDa to about 100 kDa.

73. The composition of claim 72, wherein said polyalkylene glycol of (a) has two branches, each with a molecular weight of from about 2 kDa to about 30 kDa.

74. The composition of claim 72, wherein said polyalkylene glycol of (a) has a molecular weight of from about 10 kDa to about 20 kDa.

75. The composition of claim 69, wherein said peptide, protein or glycoprotein is attached to from one to about 100 molecules of said linear or branched polyalkylene glycol(s).

76. The composition of claim 75, wherein said peptide, protein or glycoprotein is attached to from one to about five molecules of said linear or branched polyalkylene glycol(s).

77. The composition of claim 76, wherein said peptide, protein or glycoprotein is attached to one or two molecules of said linear or branched polyalkylene glycol(s).

78. The composition of claim 75, wherein said peptide, protein or glycoprotein is attached to about five to about 100 molecules of said linear or branched polyalkylene glycol(s).

79. The composition of claim 69, wherein said purified monofunctionally activated derivative of (c) is selected from the group consisting of a hydroxyPEG-monoaldehyde and a reactive ester of a hydroxyPEG-monoacid.

80. The composition of claim 69, wherein said polyalkylene glycol of (a) is a linear dihydroxyPEG.

81. The composition of claim 69, wherein said peptide, protein or glycoprotein is an allergen.

82. A pharmaceutical composition comprising the composition of claim 69 and a pharmaceutically acceptable excipient or carrier.

83. The pharmaceutical composition of claim 82, wherein said peptide, protein or glycoprotein is selected from the group consisting of an enzyme, a serum protein, a serum glycoprotein, a blood cell protein, a pigmentary protein, hemoglobin, a viral protein, a peptide hormone, a protein hormone, a glycoprotein hormone, a hypothalamic releasing factor, a cytokine and a growth factor.

84. The pharmaceutical composition of claim 83, wherein said peptide, protein or glycoprotein is a serum protein and is selected from the group consisting of an albumin, an immunoglobulin and a blood-clotting factor.

85. The pharmaceutical composition of claim 83, wherein said peptide hormone or protein hormone or glycoprotein hormone is selected from the group consisting of an antidiuretic hormone, chorionic gonadotropin, luteinizing hormone, follicle-stimulating hormone, insulin, prolactin, a somatomedin, growth hormone, thyroid-stimulating hormone and a placental lactogen.

86. The pharmaceutical composition of claim 83, wherein said peptide, protein or glycoprotein is a growth factor and is selected from the group consisting of a colony-stimulating factor, an epidermal growth factor, an erythropoietin, a fibroblast growth factor, an insulin-like growth factor, a transforming growth factor, a platelet-derived growth factor, a nerve growth factor, a hepatocyte growth factor, a neurotrophic factor, a ciliary neurotrophic factor, a brain-derived neurotrophic factor, a glial-derived neurotrophic factor and a bone morphogenic peptide.

87. The pharmaceutical composition of claim 83, wherein said peptide, protein or glycoprotein is a cytokine and is selected from the group consisting of a lymphokine, an interleukin, an interferon, a tumor necrosis factor, a leukemia inhibitory factor and thrombopoietin.

88. The pharmaceutical composition of claim 83, wherein said peptide, protein or glycoprotein is an enzyme and is selected from the group consisting of a carbohydrate-specific enzyme, a proteolytic enzyme, an oxidoreductase, a transferase, a hydrolase, a lyase, an isomerase and a ligase.

89. The pharmaceutical composition of claim 88, wherein said enzyme is a uricase.

90. The pharmaceutical composition of claim 88, wherein said enzyme is a plasminogen activator.

91. The pharmaceutical composition of claim 83, wherein said peptide, protein or glycoprotein is a colony-stimulating factor.

92. The pharmaceutical composition of claim 91, wherein said colony-stimulating factor is a GM-CSF.

93. The pharmaceutical composition of claim 86, wherein said growth factor is an erythropoietin.

94. The composition of claim 76, wherein said peptide, protein or glycoprotein is attached to from one to three molecules of said linear or branched polyalkylene glycol(s).

* * * * *

UNITED STATES PATENT AND TRADEMARK OFFICE
CERTIFICATE OF CORRECTION

PATENT NO. : 8,129,330 B2
APPLICATION NO. : 10/669597
DATED : March 6, 2012
INVENTOR(S) : Martinez et al.

Page 1 of 1

It is certified that error appears in the above-identified patent and that said Letters Patent is hereby corrected as shown below:

In the Claims

Column 43
Line 37 "pharmacuatical" should be replaced with --pharmaceutical--

Column 44
Line 35 "moleculed" should be replaced with --molecules--

Column 45
Line 2 "growth growth factor" should be replaced with --growth factor--

Column 46
Line 42 "obtaining" should be replaced with --(a) obtaining--

Column 46
Line 44 "producing" should be replaced with --(b) producing--

Signed and Sealed this
Twelfth Day of May, 2015

Michelle K. Lee
*Director of the United States Patent and Trademark Office*